United States Patent
Amplatz et al.

(10) Patent No.: US 8,313,505 B2
(45) Date of Patent: *Nov. 20, 2012

(54) DEVICE FOR OCCLUDING VASCULAR DEFECTS

(75) Inventors: Kurt Amplatz, St. Paul, MN (US); Matt Glimsdale, St. Michael, MN (US); Jana Santer, Spring Lakae Park, MN (US); Xiaoping Gu, Plymouth, MN (US); John Oslund, Blaine, MN (US)

(73) Assignee: AGA Medical Corporation, Plymouth, MN (US)

( * ) Notice: Subject to any disclaimer, the term of this patent is extended or adjusted under 35 U.S.C. 154(b) by 375 days.

This patent is subject to a terminal disclaimer.

(21) Appl. No.: 12/040,260

(22) Filed: Feb. 29, 2008

(65) Prior Publication Data

US 2008/0200945 A1    Aug. 21, 2008

Related U.S. Application Data

(63) Continuation-in-part of application No. 11/820,841, filed on Jun. 21, 2007, which is a continuation-in-part of application No. 11/473,971, filed on Jun. 23, 2006, which is a continuation-in-part of application No. 10/804,993, filed on Mar. 19, 2004, now abandoned.

(51) Int. Cl.
*A61F 2/00* (2006.01)
(52) U.S. Cl. ..................................... 606/200
(58) Field of Classification Search .............. 606/200, 606/198, 151, 191, 194
See application file for complete search history.

(56) References Cited

U.S. PATENT DOCUMENTS

| | | | |
|---|---|---|---|
| 3,834,388 A | 9/1974 | Sauer | |
| 3,874,388 A | 4/1975 | King et al. | |
| 4,304,010 A | 12/1981 | Mano | |
| 4,441,215 A | 4/1984 | Kaster | |
| 4,655,771 A | 4/1987 | Wallsten | |
| 4,728,328 A | 3/1988 | Hughes et al. | |
| 4,836,204 A | 6/1989 | Landymore et al. | |
| 4,917,089 A | 4/1990 | Sideris | |
| 4,991,602 A | 2/1991 | Amplatz et al. | |
| 5,064,435 A | 11/1991 | Porter | |
| 5,067,489 A | 11/1991 | Lind et al. | |
| 5,108,420 A | 4/1992 | Marks | |
| 5,334,217 A | 8/1994 | Das | |
| 5,522,822 A | 6/1996 | Phelps et al. | |
| 5,522,881 A | 6/1996 | Lentz | |

(Continued)

FOREIGN PATENT DOCUMENTS

CA    2501033    7/2008

(Continued)

OTHER PUBLICATIONS

Dictionary.com, definition of "plane", retrieved Oct. 27, 2011 from the world wide web: http:dictionary.com/browse/plane.*

(Continued)

*Primary Examiner* — Ryan Severson
(74) *Attorney, Agent, or Firm* — Alston & Bird LLP

(57) ABSTRACT

Embodiments of the present invention provide devices and methods for treating abnormalities. For example, a device according to one embodiment includes a plurality of planes of occlusion, at least one plane of occlusion comprising a plurality of layers of occlusive material. The device is configured to at least partially occlude an abnormality.

36 Claims, 20 Drawing Sheets

U.S. PATENT DOCUMENTS

| | | | |
|---|---|---|---|
| 5,562,725 A | | 10/1996 | Schmitt et al. |
| 5,628,788 A | | 5/1997 | Pinchuk |
| 5,709,707 A | | 1/1998 | Lock et al. |
| 5,709,713 A | | 1/1998 | Evans et al. |
| 5,725,552 A | * | 3/1998 | Kotula et al. ............... 606/213 |
| 5,741,325 A | | 4/1998 | Chaikof et al. |
| 5,755,772 A | | 5/1998 | Evans et al. |
| 5,758,562 A | | 6/1998 | Thompson |
| 5,800,508 A | | 9/1998 | Goicoechea et al. |
| 5,846,261 A | * | 12/1998 | Kotula et al. ............... 606/213 |
| 5,865,791 A | | 2/1999 | Whayne et al. |
| 5,906,641 A | | 5/1999 | Thompson et al. |
| 5,916,264 A | | 6/1999 | Von Oepen et al. |
| 5,928,260 A | | 7/1999 | Chin et al. |
| 5,944,738 A | * | 8/1999 | Amplatz et al. ............. 606/213 |
| 5,957,974 A | | 9/1999 | Thompson et al. |
| 5,984,917 A | | 11/1999 | Fleischman et al. |
| 5,994,738 A | | 11/1999 | Wollesen |
| 6,042,592 A | | 3/2000 | Schmitt |
| 6,059,812 A | | 5/2000 | Clerc et al. |
| 6,066,776 A | | 5/2000 | Goodwin et al. |
| 6,096,052 A | | 8/2000 | Callister et al. |
| 6,110,198 A | | 8/2000 | Fogarty et al. |
| 6,123,715 A | | 9/2000 | Amplatz |
| 6,132,438 A | | 10/2000 | Fleischman et al. |
| 6,152,144 A | | 11/2000 | Lesh et al. |
| 6,156,064 A | | 12/2000 | Chouinard |
| 6,168,615 B1 | | 1/2001 | Ken et al. |
| 6,168,622 B1 | | 1/2001 | Mazzocchi |
| 6,187,025 B1 | * | 2/2001 | Machek ...................... 606/200 |
| 6,241,768 B1 | | 6/2001 | Agarwal et al. |
| 6,267,775 B1 | | 7/2001 | Clerc et al. |
| 6,299,636 B1 | | 10/2001 | Schmitt et al. |
| 6,346,117 B1 | | 2/2002 | Greenhalgh |
| 6,368,339 B1 | * | 4/2002 | Amplatz ...................... 606/200 |
| 6,379,366 B1 | | 4/2002 | Fleischman et al. |
| 6,447,531 B1 | * | 9/2002 | Amplatz ...................... 606/200 |
| 6,468,301 B1 | | 10/2002 | Amplatz et al. |
| 6,468,303 B1 | * | 10/2002 | Amplatz et al. ............... 623/1.2 |
| 6,488,705 B2 | | 12/2002 | Schmitt et al. |
| 6,494,907 B1 | | 12/2002 | Bulver |
| 6,500,203 B1 | | 12/2002 | Thompson et al. |
| 6,551,303 B1 | | 4/2003 | VanTassel et al. |
| 6,599,308 B2 | | 7/2003 | Amplatz |
| 6,652,555 B1 | | 11/2003 | VanTassel et al. |
| 6,652,556 B1 | | 11/2003 | VanTassel et al. |
| 6,682,546 B2 | | 1/2004 | Amplatz |
| 6,709,451 B1 | | 3/2004 | Noble et al. |
| 6,709,455 B1 | | 3/2004 | Chouinard |
| 6,730,108 B2 | | 5/2004 | VanTassel et al. |
| 6,773,448 B2 | * | 8/2004 | Kusleika et al. ............. 606/200 |
| 6,830,576 B2 | | 12/2004 | Fleischman et al. |
| 6,860,900 B2 | | 3/2005 | Clerc et al. |
| 6,866,679 B2 | | 3/2005 | Kusleika |
| 6,911,037 B2 | | 6/2005 | Gainor et al. |
| 6,932,837 B2 | | 8/2005 | Amplatz et al. |
| 6,949,113 B2 | | 9/2005 | VanTassel et al. |
| 6,974,586 B2 | | 12/2005 | Greenhalgh et al. |
| 7,025,779 B2 | | 4/2006 | Elliott |
| 7,029,494 B2 | | 4/2006 | Soun et al. |
| 7,044,134 B2 | | 5/2006 | Khairkhahan et al. |
| 7,052,513 B2 | | 5/2006 | Thompson |
| 7,128,073 B1 | | 10/2006 | van der Burg et al. |
| 7,147,656 B2 | | 12/2006 | Andreas et al. |
| 7,152,605 B2 | | 12/2006 | Khairkhahan et al. |
| 7,169,164 B2 | | 1/2007 | Borillo et al. |
| 7,678,123 B2 | | 3/2010 | Chanduszko |
| 2001/0000797 A1 | | 5/2001 | Mazzocchi |
| 2001/0031981 A1 | | 10/2001 | Evans et al. |
| 2002/0010481 A1 | * | 1/2002 | Jayaraman .................... 606/151 |
| 2002/0026237 A1 | | 2/2002 | Schmitt et al. |
| 2003/0055491 A1 | | 3/2003 | Schwartz et al. |
| 2003/0057156 A1 | | 3/2003 | Peterson et al. |
| 2003/0074019 A1 | * | 4/2003 | Gray et al. .................... 606/200 |
| 2003/0135265 A1 | | 7/2003 | Stinson |
| 2003/0171770 A1 | * | 9/2003 | Kusleika et al. .............. 606/200 |
| 2003/0195553 A1 | | 10/2003 | Wallace et al. |
| 2003/0199819 A1 | | 10/2003 | Beck |
| 2004/0006363 A1 | | 1/2004 | Schaefer |
| 2004/0093022 A9 | | 5/2004 | Kurz et al. |
| 2004/0143293 A1 | | 7/2004 | Marino et al. |
| 2004/0220610 A1 | | 11/2004 | Kreidler et al. |
| 2005/0033321 A1 | | 2/2005 | Fleischman et al. |
| 2005/0171572 A1 | | 8/2005 | Martinez |
| 2005/0209633 A1 | * | 9/2005 | Callister et al. .............. 606/200 |
| 2005/0216049 A1 | | 9/2005 | Jones et al. |
| 2005/0228434 A1 | | 10/2005 | Amplatz et al. |
| 2006/0100684 A1 | | 5/2006 | Elliott |
| 2006/0106419 A1 | | 5/2006 | Gingras |
| 2006/0122645 A1 | | 6/2006 | Brady et al. |
| 2006/0135947 A1 | | 6/2006 | Soltesz et al. |
| 2006/0206201 A1 | | 9/2006 | Garcia et al. |
| 2006/0241690 A1 | * | 10/2006 | Amplatz et al. .............. 606/213 |
| 2006/0247680 A1 | | 11/2006 | Amplatz et al. |
| 2006/0253184 A1 | | 11/2006 | Amplatz |
| 2006/0266474 A1 | | 11/2006 | Burnside et al. |
| 2007/0043391 A1 | | 2/2007 | Moszner et al. |
| 2007/0088384 A1 | | 4/2007 | Vrba et al. |
| 2007/0112380 A1 | | 5/2007 | Figulla et al. |
| 2007/0112381 A1 | | 5/2007 | Figulla et al. |
| 2007/0167980 A1 | | 7/2007 | Figulla et al. |
| 2007/0168018 A1 | | 7/2007 | Amplatz et al. |
| 2007/0168019 A1 | | 7/2007 | Amplatz et al. |
| 2007/0265656 A1 | * | 11/2007 | Amplatz et al. .............. 606/200 |
| 2007/0265658 A1 | | 11/2007 | Nelson et al. |
| 2008/0015628 A1 | | 1/2008 | Dubrul et al. |
| 2008/0221554 A1 | | 9/2008 | O'Connor et al. |
| 2009/0018562 A1 | * | 1/2009 | Amplatz et al. .............. 606/157 |
| 2009/0143814 A1 | | 6/2009 | Gilson et al. |
| 2009/0171386 A1 | * | 7/2009 | Amplatz et al. .............. 606/213 |
| 2009/0187214 A1 | * | 7/2009 | Amplatz et al. .............. 606/213 |
| 2010/0121370 A1 | * | 5/2010 | Kariniemi .................... 606/191 |
| 2011/0184508 A2 | | 7/2011 | Burmeister et al. |

FOREIGN PATENT DOCUMENTS

| | | |
|---|---|---|
| DE | 103 38 702 B3 | 3/2005 |
| EP | 1 576 929 A2 | 9/2005 |
| JP | 4020308 U | 2/1992 |
| JP | 2001-515748 A | 9/2001 |
| JP | 2002-119515 A | 4/2002 |
| JP | 2005-261951 A | 9/2005 |
| JP | 2005-528181 A | 9/2005 |
| WO | WO 96/01599 A1 | 1/1996 |
| WO | WO 97/31672 | 9/1997 |
| WO | WO 99/12478 A1 | 3/1999 |
| WO | WO 99/39646 A1 | 8/1999 |
| WO | WO 00/13624 A2 | 3/2000 |
| WO | WO 00/28923 A1 | 5/2000 |
| WO | WO 01/72367 A1 | 10/2001 |
| WO | WO 2007/087005 A2 | 8/2007 |

OTHER PUBLICATIONS

U.S. Appl. No. 11/827,590, filed Jul. 12, 2007.
U.S. Appl. No. 11/966,397, filed Dec. 28, 2007, Adams et al.

\* cited by examiner

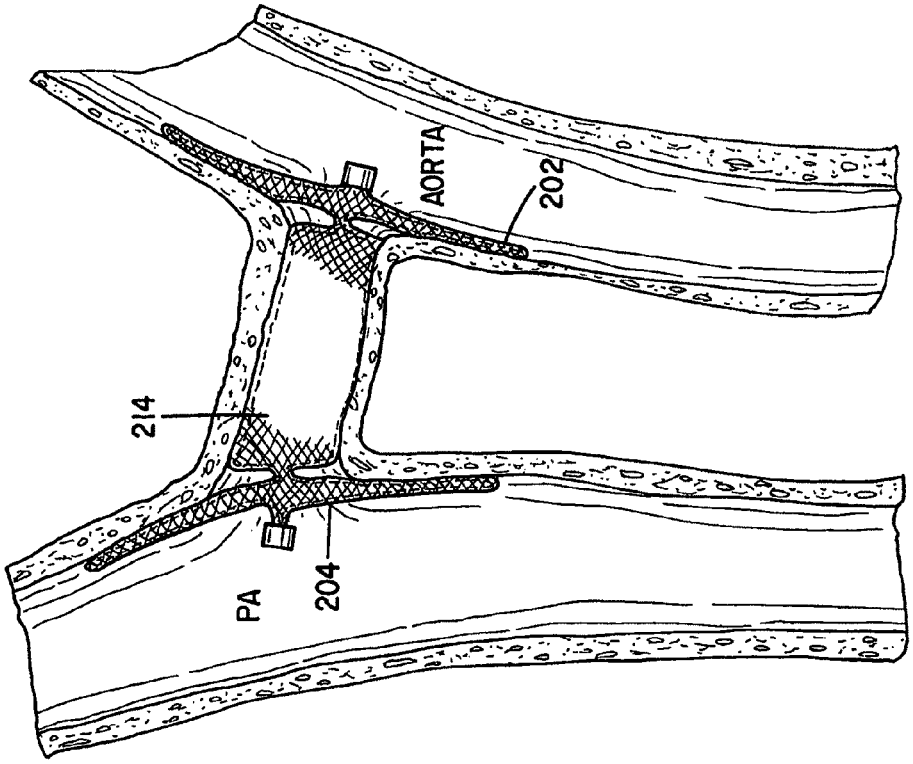
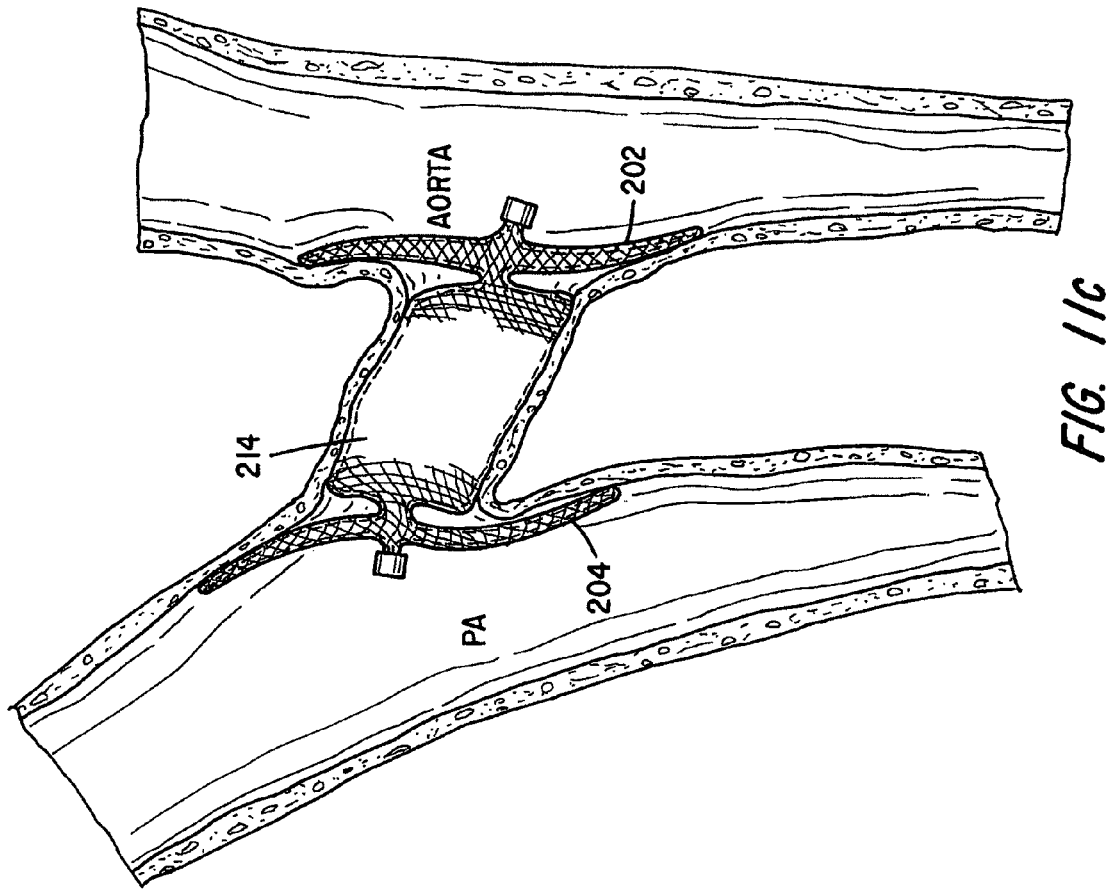
FIG. 11d
FIG. 11c

DEVICE FOR OCCLUDING VASCULAR DEFECTS

CROSS REFERENCE TO RELATED APPLICATIONS

This application is a continuation-in-part of U.S. application Ser. No. 11/820,841 filed Jun. 21, 2007, which is a continuation-in-part of U.S. application Ser. No. 11/473,971 filed Jun. 23, 2006, which is a continuation-in-part of U.S. application Ser. No. 10/804,993 filed Mar. 19, 2004, now abandoned each of which is incorporated in its entirety herein.

BACKGROUND OF THE INVENTION

I. Field of the Invention

The present invention generally relates to devices for treating various medical conditions and, more particularly, relates to occlusion devices for treating various abnormalities within a patient's body.

II. Description of the Related Art

A wide variety of intracardiac prosthetic devices are used in various medical procedures. For example, certain intravascular devices, such as catheters and guide wires, are generally used to deliver fluids or other medical devices to specific locations within the vascular system of a patient, such as a selective coronary artery. Other devices are used in treating specific conditions, such as devices used in removing vascular occlusions or for treating septal defects and the like. For example, devices have been developed for treating abnormalities, such as an Atrial Septal Defect (ASD), a Ventricular Septal Defect (VSD), a Patent Ductus Arteriosus (PDA), a Patent Foramen Ovale (PFO), as well as conditions that result from previous medical procedures such as Para-Valvular Leaks (PVL) following surgical valve repair or replacement.

However, the ability to deliver these devices to particular areas of the vasculature or for particular patients may be limited by their bulkiness. Previous devices typically require a 14-16 French introducing catheter, which generally makes it impossible to treat children affected with congenital defects with these devices. With respect to a PDA, a smaller, lower profile device that can fit through a 4 French catheter potentially allows treatment of pre-mature infants with a PDA. Moreover, some of these devices are used to occlude a patient's vessel or abnormality, such as to stop blood flow through an artery to a tumor or other lesion. Despite the general ability to occlude a vessel or abnormality, reducing the time needed to occlude the vessel or abnormality is desired so that the device may be accurately and effectively positioned and fixated within the vessel.

Accordingly, it would be advantageous to provide a reliable occlusion device which is both easy to deploy through a catheter having a reduced diameter and that can be accurately placed in a vessel or an organ. It would also be desirable to provide a low-profile recoverable device for deployment in a vessel or an organ of a patient's body. In addition, there exists a need for a collapsible medical device for occluding abnormal openings in an vessel or organ which provides rapid occlusion following delivery and placement thereof. Moreover, there is also a need for an occlusion device that may be effectively fixated within a vessel or an organ.

SUMMARY OF THE INVENTION

Embodiments of the present invention may provide improvements over the prior art by, among other things, providing devices and methods for treating abnormalities. For example, a device according to one embodiment includes a plurality of planes of occlusion, wherein at least one plane of occlusion includes a plurality of layers of occlusive material, and wherein the planes of occlusion are configured to at least partially occlude an abnormality. The device may be configured to be delivered through a catheter having an outer diameter of less than 9 French for percutaneous delivery to the abnormality and, in one embodiment, less than 4 French. In addition the device may be configured to occlude an abnormality within less than 10 minutes and, in one embodiment, less than 3 minutes. Thus, the device may be constrained to a smaller diameter than conventional devices for treating abnormalities and may more rapidly occlude abnormalities.

According to aspects of the present invention, the medical device may comprise a plurality of planes of occlusion, such as at least four planes of occlusion. The planes of occlusion may be oriented generally transverse to the flow of blood to facilitate the formation of thrombus. In addition, at least one of the plurality of planes of occlusion may include a layer of occlusive material (e.g., layer of braided metal fabric such as Nitinol), such as at least two layers of occlusive material. At least one plane of occlusion may be configured to be positioned within a vessel or an organ and overlie an opening of the abnormality, and at least one plane of occlusion may be configured to be at least partially positioned within the opening defined by the abnormality. For example, at least one of the plurality of planes of occlusion may be configured to be positioned within a first vessel or an organ, at least one of the plurality of planes of occlusion may be configured to be positioned within a second vessel or an organ, and at least one of the plurality of layers of occlusion may be configured to be positioned within an opening extending between the first and second vessels or organs. One or more of the plurality of planes of occlusion may be round, oval, crescent, non-circular, or other shape, and the plurality of planes of occlusion may be configured to be oriented generally transverse to the flow of blood so as to facilitate the formation of thrombus. Moreover, the medical device may be configured for delivery over a guide wire.

An additional aspect of the present invention provides a method for occluding an abnormality with a medical device having a plurality of planes of occlusion, wherein at least one of the planes of occlusion includes a plurality of layers of occlusive material. The method includes constraining a medical device to a smaller diameter than an expanded preset configuration, delivering the medical device proximate to the abnormality, and deploying the medical device proximate to the abnormality such that the plurality of planes of occlusion at least partially occlude the abnormality.

Aspects of the method include constraining the medical device by stretching the medical device along a longitudinal axis thereof to the smaller diameter. The deploying step may include deploying the medical device such that at least one of the plurality of planes of occlusion is configured to overlie an opening of the abnormality, or deploying the medical device such that at least one of the plurality of layers of occlusion is at least partially positioned within an opening defined by the abnormality. The delivering step may include delivering the medical device over a guide wire. In addition, the deploying step may include deploying the medical device such that the plurality of planes of occlusion are oriented generally transverse to the flow of blood so as to facilitate the formation of thrombus. The delivering step may include delivering the device arterially or venously proximate to the abnormality.

BRIEF DESCRIPTION OF THE DRAWINGS

The foregoing features and advantages of the invention will become apparent to those skilled in the art from the following detailed description of a preferred embodiment, especially when considered in conjunction with the accompanying drawings in which like numerals in the several views refer to corresponding parts.

FIGS. 11a-11f are side and end views and cross-sectional views of an occluder device according to alternative embodiment for treating a vascular abnormality;

DETAILED DESCRIPTION OF THE PREFERRED EMBODIMENTS

Figure 2:
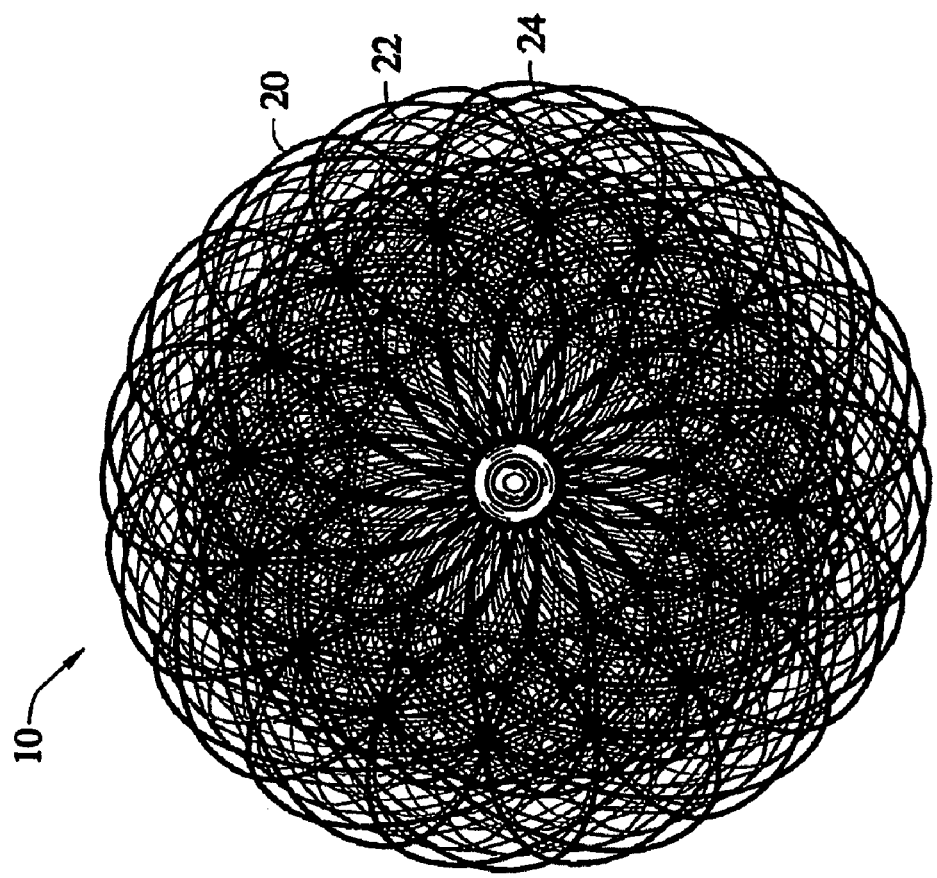
FIG. 2 is an enlarged front elevation view of the device of FIG. 1.

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Embodiments of the present invention provide an occlusion device for use in occluding an abnormality in a patients' body, such as an Atrial Septal Defect (ASD), a Ventricular Septal Defect (VSD), a Patent Ductus Arteriosus (PDA), a Patent Foramen Ovale (PFO), conditions that result from previous medical procedures such as Para-Valvular Leaks (PVL) following surgical valve repair or replacement, and the like. The device may also be used as a flow restrictor or an aneurysm bridge or other type of occluder for placement in the vascular system. It is understood that the use of the term "abnormality" is not meant to be limiting, as the device may be configured to occlude any vessel, organ, opening, chamber, channel, hole, cavity, or the like, located anywhere in the body.

According to one embodiment of the present invention for forming a medical device of the invention, the device includes a braided fabric formed of a plurality of wire strands having a predetermined relative orientation with respect to one another. However, it is understood that according to additional embodiments of the present invention, the device may be formed using various techniques. For example, the device could be etched or laser cut from a tube such as to form an interstice geometry, or the device could comprise an occlusion material coupled to a scaffolding structure or a plurality of slices of a tubular member coupled together, such as via gluing. Moreover, it is understood that the device may comprise one or more layers of occluding material such that the device may be a variety of occluding materials capable of at least partially inhibiting blood flow therethrough in order to facilitate the formation of thrombus and epitheliazation around the device.

Although the term "strand" is discussed herein, "strand" is not meant to be limiting, as it is understood the fabric may comprise one or more wires, cords, fibers, yarns, filaments, cables, threads, or the like, such that such terms may be used interchangeably.

As used herein, "substantially preclude or impede flow" shall mean, functionally, that blood flow may occur for a short time, e.g., about 3-60 minutes through the occlusive material, but that the body's clotting mechanism or protein or other body deposits on the braided wire strands results in occlusion or flow stoppage after this initial time period. For instance, occlusion may be clinically represented by injecting a contrast media into the upstream lumen of the device and if no contrast media flows through the wall of the device after a predetermined period of time as viewed by fluoroscopy, then the position and occlusion of the device is adequate. Moreover, occlusion of the vascular abnormality could be assessed using various echo modalities. According to one embodiment of the present invention, the device is configured to occlude at least a portion of the PDA in less than about 4 minutes.

As used herein the term "proximal" shall mean closest to the operator (less into the body) and "distal" shall mean furthest from the operator (further into the body). In positioning of the medical device from a downstream access point, distal is more upstream and proximal is more downstream.

According to one embodiment, the occlusive material is a metal fabric including a plurality of strands, such as two sets of essentially parallel generally helical strands, with the strands of one set having a "hand", i.e., a direction of rotation, opposite that of the other set. The strands may be braided, interwoven, or otherwise combined to define a generally tubular fabric.

The pitch of the strands (i.e., the angle defined between the turns of the strands and the axis of the braid) and the pick of the fabric (i.e., the number of wire strand crossovers per unit length) may be adjusted as desired for a particular application. The wire strands of the metal fabric used in one embodiment of the present method may be formed of a material that is both resilient and can be heat treated to substantially set a desired shape. One factor in choosing a suitable material for the wire strands is that the wires retain a suitable amount of the deformation induced by the molding surface (as described below) when subjected to a predetermined heat treatment and elastically return to said molded shape after substantial deformation.

One class of materials which meets these qualifications is so-called shape memory alloys. One particularly preferred shape memory alloy for use in the present method is Nitinol. NiTi alloys are also very elastic—they are said to be "superelastic" or "pseudoelastic". This elasticity may allow the device to return to a preset expanded configuration for deployment following passage in a distorted form through a delivery catheter. It is also understood that the device may comprise various materials other than Nitinol that have elastic properties, such as spring stainless steel, trade named alloys such as Elgiloy, or Hastalloy, Phynox, MP35N, CoCrMo alloys or a mixture of metal and polymer fibers. Polymer fibers may include monofilaments or multifilament yarns ranging from about 10-400 denier. Individual filaments may range from about 0.25 to 10 denier. Polymers may be composed of PET (Dacron), polyester, polypropylene, polyethylene, HDPE, polyurethane, silicone, PTFE, polyolefins and ePTFE. The metal and plastic fibers may be combined in the same layer, or the tubular layers may be constructed in such a manner that each layer is made from a different material. The polymer layer may be a multifilament braided layer or may be composed of at least one filament or yarn wound about a mandrel with a pitch and diameter similar to other adjacent layers and may be positioned about or inside another adjacent layer or between adjacent layers. Depending on the individual material selected, the wire strand diameter, number of wire strands and pitch may be altered to achieve the desired properties of the device. Moreover, other suitable materials include those that are compatible with magnetic resonance imaging (MRI), as some materials may cause heat or torque resulting from performing MRI, and some materials may distort the MRI image. Thus, metallic and/or non-metallic materials that reduce or eliminate these potential problems resulting from using MRI may be employed.

In forming a medical device according to one embodiment of the present invention, an appropriately sized piece of the fabric is cut from the larger piece of fabric which is formed, for example, by braiding wire strands to form a long tubular braid. When cutting the fabric to the desired dimensions, care should be taken to ensure that the fabric will not unravel. One can solder, braze, weld, coat, glue, clamp, tie or otherwise affix the ends of the desired length together (e.g., with a biocompatible cementitious organic material).

In addition, a plurality of layers of occlusive material could be separately woven into tubular members, with each tubular member coaxially disposed within another tubular member. For further discussion regarding an exemplary multi-layer device and techniques for fabricating such a device, see U.S. Patent Appl. Publ. No. 2007/0265656 to Amplatz et al., which is hereby incorporated in its entirety by reference.

According to one embodiment, each layer of the device may comprise 36-144 wire strands ranging in diameter from about 0.001 to 0.012 in. formed of a shape memory alloy, such as Nitinol, that are braided so as to define fenestrations with an area of about 0.00015 to 0.1 sq. in., which are sufficiently small so as to slow the blood flow through the wall of the device and to facilitate thrombus formation thereon. Inner and outer braided layers may have pitch angles that are about equal to obtain desirable collapse and expansion characteristics, such as maintaining a uniform overall length.

Once an appropriately sized piece of the metal fabric is obtained, the fabric is deformed to generally conform to a surface of a molding element. Deforming the fabric will reorient the relative positions of the wire strands of the metal fabric from their initial order to a second, reoriented configuration. The shape of the molding element should be selected to deform the fabric into substantially the shape of the desired medical device when unconstrained. Once the molding element is assembled with the metal fabric generally conforming to a molding surface of that element, the fabric can be subjected to a heat treatment while it remains in contact with that molding surface. After the heat treatment, the fabric is removed from contact with the molding element and will substantially retain its shape in a deformed state.

Those skilled in the art will appreciate that in order to speed up the occlusion of the vessel device, the device may be coated with a suitable thrombogenic agent, filled with a polyester fiber, braided with an increased number of wire strands, or include multiple layers of fabric. The interwoven fiber may attach to a clot to retain the clot firmly within the device as it forms the occlusion.

The device may include a plurality of planes of occlusion. A plane of occlusion may be any surface, whether flat or irregular in shape, that may be oriented generally transverse to the flow of blood so as to facilitate the formation of thrombus. For example, an umbrella shaped plane, even with two layers adhered together on the front and back of a skeleton frame, would be projected as one plane of occlusion on each side of the umbrella. Whereas a device with two umbrella structures, each with their own occlusive material adhered thereto, would project into two planes of occlusion for each umbrella. At least one plane of occlusion may include one or more layers of occlusive material, such as a layer of fabric and/or a layer of polyester fiber, two layers of metal, or two layers of polyester. Thus, by modifying the configuration of the device, the number of planes of occlusion may be modified, and by changing the number of layers of occlusive material, the rate at which the device occludes the vascular abnormality may also be modified. For example, the device 10 shown in FIG. 1 has four planes of occlusion, with each plane comprising at least two layers of occlusive material.

Once a device having a preselected shape has been formed, the device may be used to treat a physiological condition of a patient. A medical device suitable for treating the condition, which may be substantially in accordance with one of the embodiments outlined below, is selected. Once the appropriate medical device is selected, a catheter or other suitable delivery device may be positioned within a channel in a patient's body to place the distal end of the delivery device adjacent the desired treatment site, such as immediately adjacent (or even within) the shunt of an abnormal opening in the patient's organ for example.

The delivery device (not shown) can take any suitable shape, such as an elongate flexible metal shaft or hypotube or metal braided polymer tube having a threaded distal end for engagement with a threaded bore formed in the clamp of the medical device. The delivery device can be used to urge the medical device through the lumen of a catheter/sheath for deployment in a channel of a patient's body. When the medical device is deployed out the distal end of the catheter, the delivery device still will retain it. Once the medical device is properly positioned within the shunt of the abnormal opening, the shaft of the delivery device can be rotated about its axis to unscrew the medical device from the delivery device.

In one embodiment the occluder device, the delivery catheter and catheter/sheath accommodate a coaxial guidewire that slideably passes through the device, end clamps and delivery catheter central lumen, and therefore helps guide the delivery device and outer catheter/sheath to the desired location. The guidewire may be delivered independently through the vasculature and across the targeted treatment location or may be extended partially distal to the distal end of the delivery device and catheter/sheath and advanced with the delivery device and catheter/sheath while the guidewire is manipulated to guide the occluder to the desired location. In another embodiment, the catheter/sheath is steerable to assist in placement of the delivery device and occluder. For further discussion regarding a delivery device and methods that may be used to deploy a device according to various aspects of the present invention, see U.S. patent application Ser. No. 11/966,397 to Adams et al., which is hereby incorporated in its entirety by reference.

By keeping the medical device attached to the delivery device, the operator can retract the device for repositioning relative to the abnormal opening, if it is determined that the device is not properly positioned within the shunt. A threaded clamp attached to the medical device allows the operator to control the manner in which the medical device is deployed out the distal end of the catheter. When the medical device exits the catheter, it will tend to resiliently return to a preferred expanded shape, which is set when the fabric is heat-treated. When the device springs back into this shape, it may tend to act against the distal end of the catheter effectively urging itself forward beyond the end of the catheter. This spring action could conceivably result in improper positioning of the device if the location of the device within a channel is critical, such as where it is being positioned in a shunt between two vessels. Since the threaded clamp can enable the operator to maintain a hold on the device during deployment, the spring action of the device can be controlled by the operator to ensure proper positioning during deployment.

The medical device can be collapsed into its reduced diameter configuration and inserted into the lumen of the catheter. The collapsed configuration of the device may be of any shape suitable for easy passage through the lumen of a catheter and proper deployment out the distal end of the catheter. For example, the device may have a relatively elongated collapsed configuration wherein the device is stretched along its axis. This collapsed configuration can be achieved simply by stretching the device generally along its axis, e.g. by manually grasping the clamps and pulling them apart, which will tend to collapse the expanded diameter portions of the device inwardly toward the device's axis. In this regard, these devices are not unlike "Chinese handcuffs", which tend to constrict in diameter under axial tension.

If the device is to be used to permanently occlude a channel in the patient's body, one can simply retract the catheter and remove it from the patient's body. This will leave the medical device deployed in the patient's vascular system so that it may occlude the blood vessel or other channel in the patient's body. In some circumstances, the medical device may be attached to a delivery system in such a manner as to secure the device to the end of the delivery means. Before removing the catheter in such a system, it may be necessary to detach the medical device from the delivery means before removing the catheter and the delivery means.

Although the device will tend to resiliently return to its initial expanded configuration, i.e., its shape prior to being collapsed for passage through the catheter, it should be understood that it might not always return entirely to that shape. For example, it may be desirable that the device has a maximum outer diameter in its expanded configuration at least as large as and preferably larger than, the inner diameter of the lumen of the abnormal opening in which it is to be deployed. If such a device is deployed in a vessel or abnormal opening having a small lumen, engagement with the lumen will prevent the device from completely returning to its expanded configuration. Nonetheless, the device would be properly deployed because it would engage the inner wall of the lumen to seat the device therein.

When the device is deployed in a patient, thrombi will tend to collect on the surface of the wires. By having a greater wire density and smaller flow passages between wires as afforded by the multiple layer construction of the present invention, the total surface area of the wires and flow resistance will be increased, increasing the thrombotic activity of the device and permitting it to relatively rapidly occlude the vessel in which it is deployed.

The device may be delivered and properly placed using two dimensional ICE, MRI, transesphogeal echocardiograpy, angiography, and/or Doppler color flow mapping. With the advent of two dimensional ICE, MRI, trans-esophageal echocardiography, bi-plane angiography, and Doppler color flow mapping, the approximate anatomy of the defect can be visualized. The device that is employed will be based on the approximate size of the vessel or abnormality to be occluded.

Figure 1:
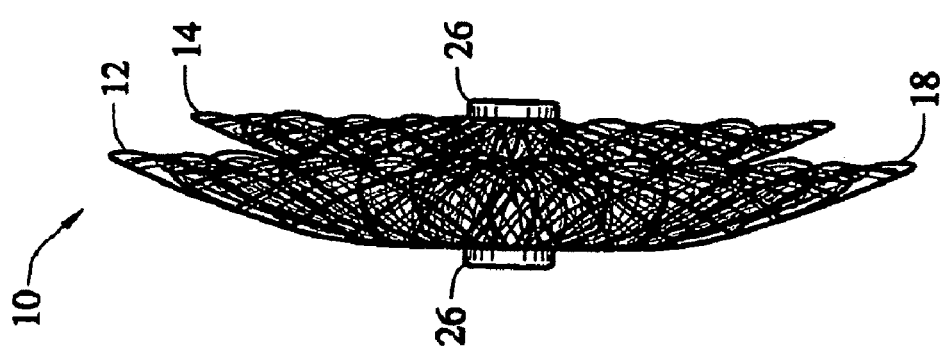
FIG. 1 is an enlarged, side elevation view of an occluder device according to one embodiment of the present invention.
Figure 4:
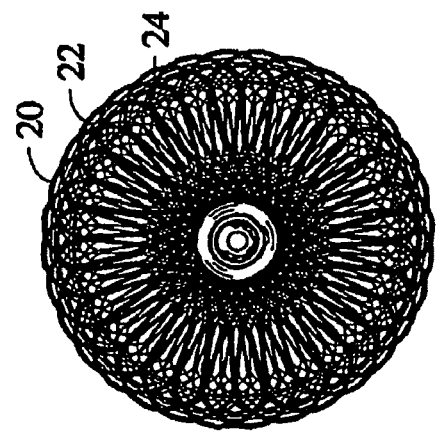
FIG. 4 is a right end view of the device shown in FIG. 3.
Figure 3:
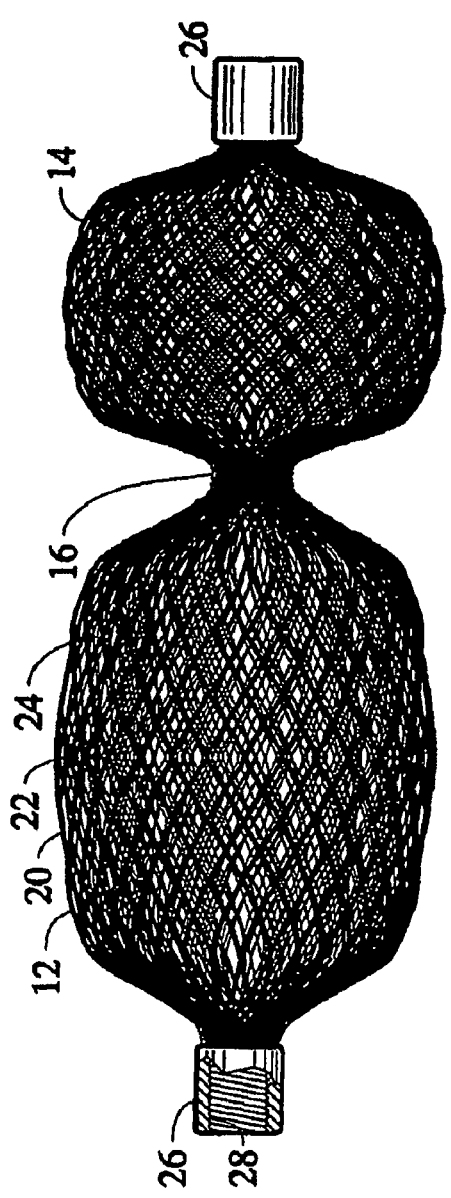
FIG. 3 is an enlarged side elevation view of the device of FIG. 1 when longitudinally stretched.

Referring now to the drawings, a discussion of the embodiments of the medical device of the present invention will next be presented. FIGS. 1-4 illustrate a first embodiment of a medical device 10 for treating a vascular abnormality, such as an ASD. The device 10 is shown in FIGS. 1 and 2 in its relaxed, non-stretched state with two aligned disks 12 and 14 linked together by a short middle cylindrical section 16 (FIG. 3). This device 10 may also be well suited in occluding defects such as a PFO. Those skilled in the art will appreciate that a device of this configuration may also be suitable for use in a transcatheter closure during a Fenestrated Fontan's procedure.

The device 10 is sized in proportion to the shunt to be occluded. In the relaxed orientation, the fabric is shaped such that two disk like members 12 and 14 are axially aligned and linked together by the short cylindrical segment 16 (i.e., 4 planes of occlusion). The length of the cylindrical segment 16 when not stretched may approximate the thickness of the atrial septum and may range, for example, between 3 to 5 mm. The proximal disk 12 and distal disk 14 may have an outer diameter sufficiently larger than the shunt to prevent dislodging of the device. The proximal disk 14 has a relatively flat configuration, whereas the distal disk 12 may be cupped towards the proximal end slightly overlapping the proximal disk 14. In this manner, the spring action of the device 10 will cause the perimeter edge 18 of the distal disk to fully engage the sidewall of the septum and likewise an outer edge of the proximal disk 14 will fully engage an opposite sidewall of the septum. Perimeter edge 18 of disk 12 as well as the perimeter edge of disk 14 may alternatively be configured with a larger radius outer edge compared to that shown in FIG. 1, to diminish forces on the tissue abutting the device.

In accordance with one embodiment of the present invention, the device 10 includes an outer braided layer 20, a first inner layer 22 and an optional third and innermost layer 24, thereby significantly increasing the wire density without unduly increasing the stiffness of the device or its ability to assume a decreased outer diameter upon longitudinal stretching. The ends of the tubular braided metal fabric device 10 may be welded or clamped together with clamps as at 26, to avoid fraying. The ends of all of the layers may be grouped together and secured by two clamps 26, one at each end or separate clamps can be applied on each end of the individual layers. The clamp 26 tying together the wire strands of the multiple layers at one end may also serve to connect the device to a delivery system, as described above. In the embodiment shown in FIG. 1, the clamp 26 is generally cylindrical in shape and has a recess (not shown) for receiving the ends of the metal fabric to substantially prevent the wires comprising the woven fabric from moving relative to one another. The clamp 26 also has a threaded bore 28. The threaded bore is adapted to receive and engage a threaded distal end of a delivery device, such as a pusher wire.

FIG. 3 illustrates the ASD device 10 in a somewhat longitudinally stretched state. The distance separating the distal and proximal disks 12 and 14 is preferably equal or slightly less than the length of the cylindrical segment 16. The cup shape of each disk 12 and 14, ensures complete contact between the outer edge of each disk 12 and 14 and the atrial septum. Upon proper placement, a new endocardial layer of endothelial cells may form over the occlusion device 10, thereby reducing the chance of bacterial endocarditic and thromboembolisms.

The distance separating the disks 12 and 14 of occluding device 10 may be increased to thereby provide an occluding device suitable for use in occluding a channel within a patient's body, having particular advantages in use as a vascular occlusion device. The relative sizes of the tubular middle section 16 and the expanded diameter portions 12, 14 can be varied as desired. The medical device can be used as a vascular occlusion device to substantially stop the flow of blood through a patient's blood vessel. When the device 10 is deployed within a patient's blood vessel, it is positioned within the vessel such that its longitudinal axis generally coincides with the axis of the vessel segment in which it is being inserted. The dumbbell shape is intended to limit the ability of the vascular occlusion device to turn at an angle with respect to the axis of the blood vessel to ensure that it remains in substantially the same position in which the operator deploys it within the vessel.

In order to position and ensure proper fixation within the lumen of the blood vessel, the maximum diameter of the expanded diameter portions 12, 14 should be selected so that it is at least as great as the diameter of the lumen of the vessel in which it is to be deployed and preferably slightly greater than that diameter. When the device is deployed within the patient's vessel, the vascular occlusion device will engage the lumen at two spaced apart locations. The device may be longer along its axis than the dimensions of its greatest diameter. This may substantially prevent the vascular occlusion device 10 from turning within the lumen at an angle to its axis, essentially preventing the device from becoming dislodged and tumbling along the vessel within the blood flowing through the vessel.

The relative sizes of the generally tubular middle portion 16 and expanded diameter portions 12, 14 of the vascular occlusion device can be varied as desired for any particular application by appropriate selection of a mold to be used during the heat setting of the device. For example, the outer diameter of the middle portion 16 may range between about ¼ and about ⅓ of the maximum diameter of the expanded diameter portions and the length of the middle portion 16 may comprise about 20% to about 50% of the overall length of the device 10. Although these dimensions are suitable if the device is to be used solely for occluding a vascular vessel, it is to be understood that these dimensions may be varied if the device is to be used in other applications, such as a VSD.

The aspect ratio (i.e., the ratio of the length of the device over its maximum diameter or width) of the device 10 illustrated in this embodiment is desirably at least about 1.0, with a range of about 1.0 to about 3.0 being preferred and then aspect ratio of about 2.0 being particularly preferred. Having a greater aspect ratio will tend to prevent the device 10 from rotating generally perpendicularly to its axis, which may be referred to as an end-over-end roll. So long as the outer diameter of the expanded diameter portions 12, 14 of the device 10 is large enough to seat the device fairly securely against the lumen of the channel in which the device is deployed, the inability of the device to turn end-over-end will help keep the device deployed precisely where it is positioned within the patient's vascular system or in any other channel in the patient's body. Alternatively, having expanded diameter portions 12, 14 which have natural relaxed diameters substantially larger than a lumen of the vessels in which the device is deployed should also suffice to wedge the device into place in the vessel without undue concern being placed on the aspect ratio of the device.

Figures 5, 6:
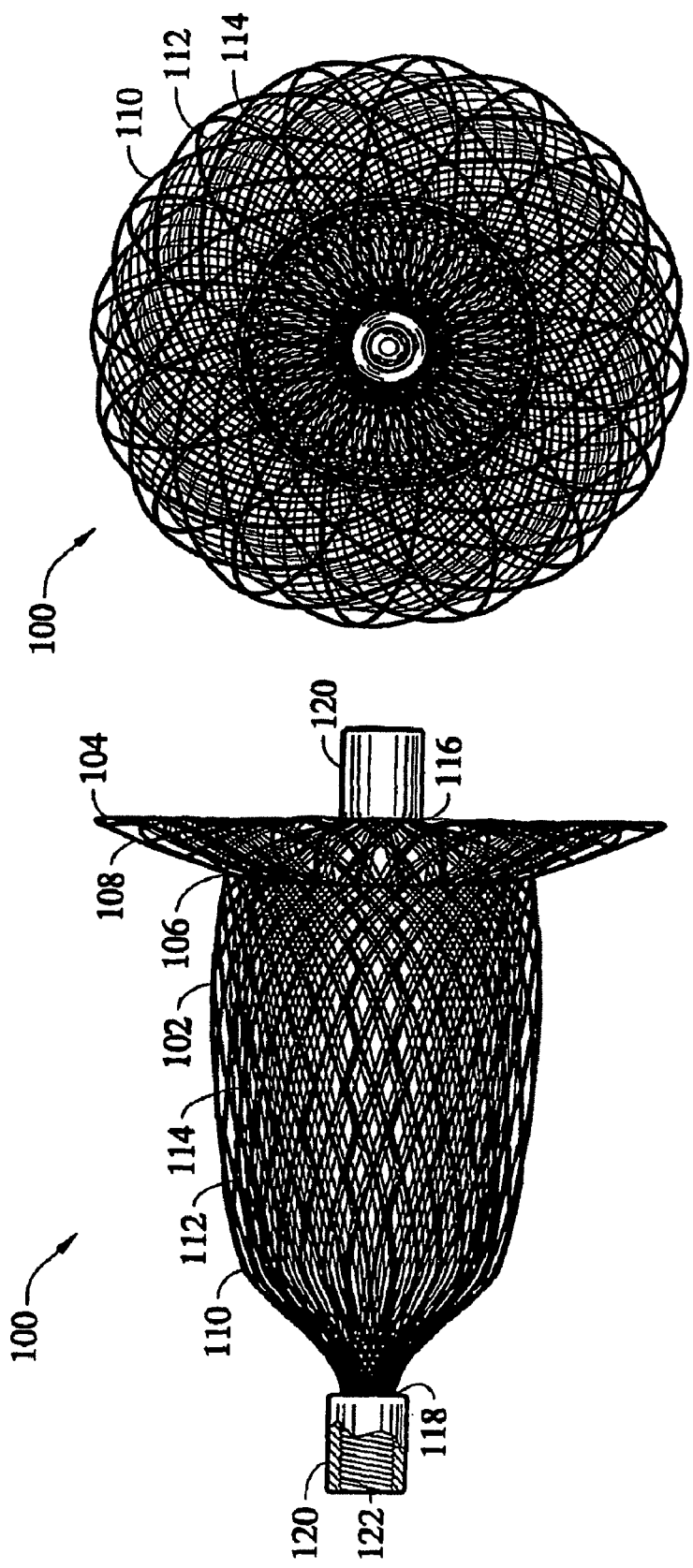
FIG. 5 is an enlarged, side elevation view of an occluder device according to an embodiment of the present invention.
FIG. 6 is a right end view of the device of FIG. 5.
Figure 7:
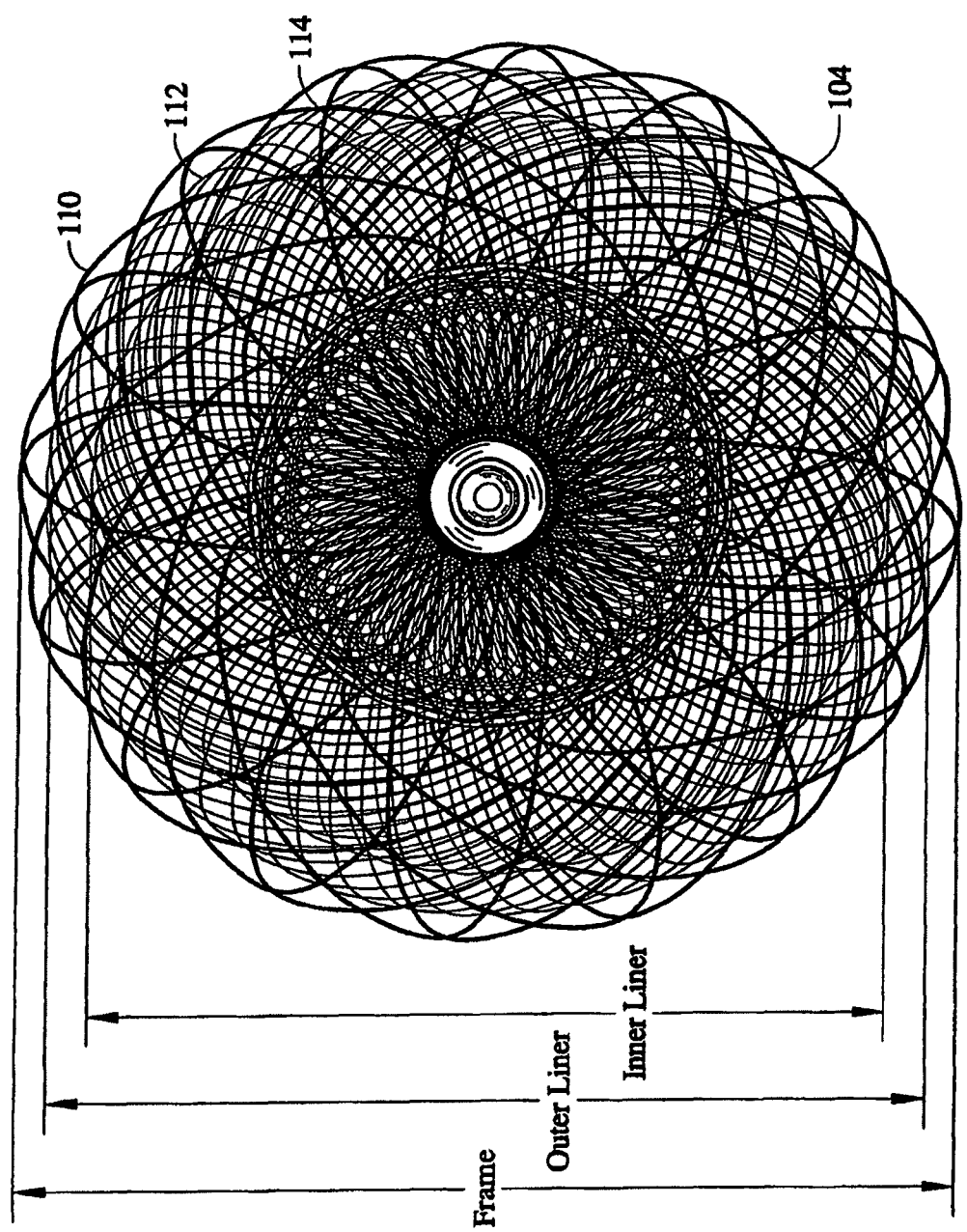
FIG. 7 is a enlarged view like that of FIG. 6.

Referring next to FIGS. 5-7, there is shown generally a device 100 suitable for occluding a PDA according to one embodiment of the present invention. The PDA device 100 has a generally bell-shaped body 102 and an outwardly flaring forward end 104. The bell-shaped body 102 is adapted to be positioned within the aorta to help seat the body of the device in the shunt. The base 106 flares out relatively rapidly to define a shoulder 108, tapering radially outwardly from the body 102. When the device 100 is deployed in a vessel, this shoulder 108 is configured to abut the perimeter of the lumen being treated with higher pressure. The forward end 104 is retained within the vessel and urges the base of the body 102 open to ensure that the shoulder 108 engages the wall of the vessel to prevent the device from becoming dislodged from within the shunt. The sizes of the body 102 and the end portion 104 can be varied as desired during manufacture to accommodate different sized shunts. For example, the body 102 may have a diameter along its generally slender middle of about 10 mm and a length along its axis of about 25 mm. In such a medical device 100, the base of the body may flare generally radially outward until it reaches an outer diameter equal to that of the forward end 104 which may be on the order of about 20 mm in diameter.

With reference to the enlarged view of FIG. 7, the outer layer 110 comprises a frame that defines the outer shape of the medical device 100. Within the frame is a layer 112 that forms an outer liner. There may also be a third layer 114 incorporated as an inner liner. According to one embodiment, clamps 120 may be used to tie together the respective ends of the wire strands on each end 116 and 118 of the tubular braid members forming the occlusion device 100 as described above. Alternatively, different clamps may be used to secure the ends of the metal strands of the outer fabric layer than are used to secure the ends of the metal strands of each of the inner layers. One or both clamps 120 of the outer layer may include a threaded bore 122 that serves to connect the device 100 to a delivery system (not shown).

Figure 8:
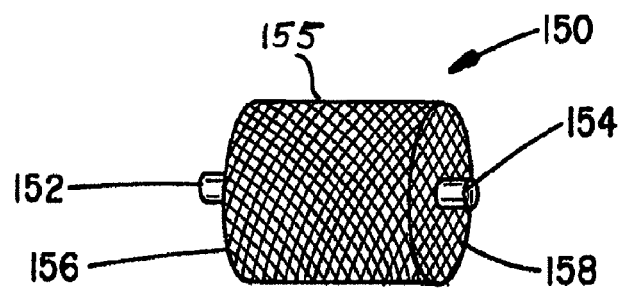
FIG. 8 shows a multi-layered vascular plug according to an embodiment of the present invention.
Figure 9:
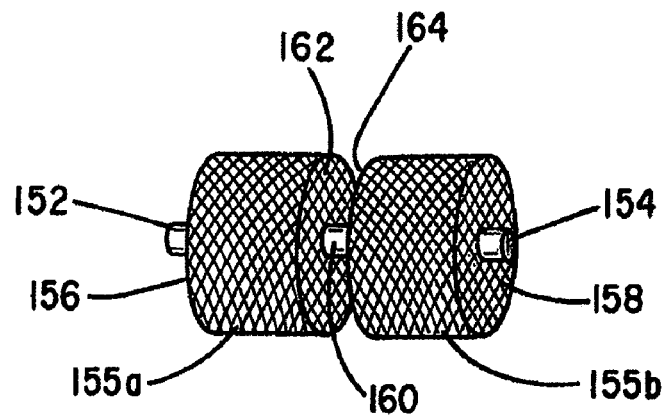
FIG. 9 shows the plug of FIG. 8 in combination with a center clamp.
Figure 10:
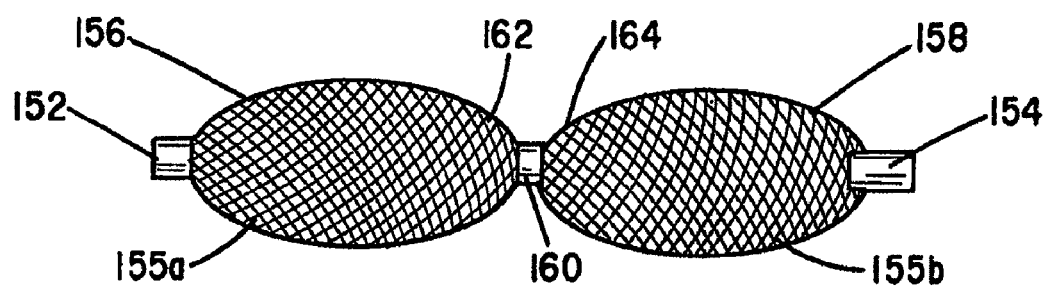
FIG. 10 shows an alternative occluder edical device according to an additional embodiment of the present invention.

FIGS. 8-10 show various devices according to additional embodiments of the present invention, which may be suited for treating a variety of arterial-venous malformations and aneurysms. These devices can also be used to block blood flow to a tumor or lesion. Likewise, these devices can be used to block fluid flow through a portion of the vasculature of the body in connection with the treatment of other medical conditions. Each embodiment shown in FIGS. 8-10 may have a multi-layered braided structure 150, i.e., two or more layers of braided fabric. When the multi-layered braided structure has a tubular shape, a pair of end clamps 152 and 154 are provided to prevent the multi-layered braided structure from unraveling. Those skilled in the art will recognize that only a single end clamp is required if the braids are in the form of a sack as opposed to having a tubular shape.

The embodiment shown in FIG. 8 has a cylindrical wall 155 with two faces 156 and 158 at the opposite ends (i.e., two planes of occlusion). Generally, when the device is in its expanded configuration as shown in FIG. 8, the cylindrical wall abuts the wall of the vessel in which the device is deployed to hold the device in place. The two faces 156 and 158 preclude fluid flow past the device.

In some treatment situations, it may be desirable to increase the number of faces to increase the ability of the device to occlude blood flow therethrough. For example, the device shown in FIG. 9 has a cylindrical wall 155, a proximal face 156, and a distal face 158. The embodiment of FIG. 9 further provides an intermediate clamp 160 clamping an intermediate portion of the fabric material. This divides the cylindrical wall into two sections 155a and 155b and forming two additional faces 162 and 164 (i.e., four planes of occlusion). When the device of FIG. 9 is deployed, the two sections 155a and 155b of cylindrical wall 155 still abuts the vessel wall to hold the device in place yet fluid must to traverse all four faces (namely faces 156, 158, 162 and 164) to flow past the device. The reduction in flow provided by the two additional faces 162 and 164 can result in faster clotting. The device shown in FIG. 10 has a similar configuration as the device shown in FIG. 9. However, the two sections 155a and 155b have a bulbous configuration rather than a cylindrical form. The widest part of sections 155a and 155b engage the vessel wall and hold the device in place after deployment.

The intermediate clamp 160 can be made of any suitable material. Suture thread has proven to be effective. The two end clamps 152 and 154 are preferably made of a radiopaque material so they can easily be visualized using, for example, a fluoroscope. The intermediate clamp can be made of such material as well. Also, additional intermediate clamps can be added to further increase the number of faces. For example, if two intermediate clamps are used, a total of six faces would be present. With each additional clamp, two additional faces are provided. Also, when the multi-layered braided structure (or at least one of the layers thereof) is made of a superelastic or shape memory material, it may be possible to eliminate the intermediate clamps and instead mold the device to have such a shape (e.g., a shape such as that shown in FIG. 8) when fully deployed and in its expanded preset configuration.

Figure 11A:
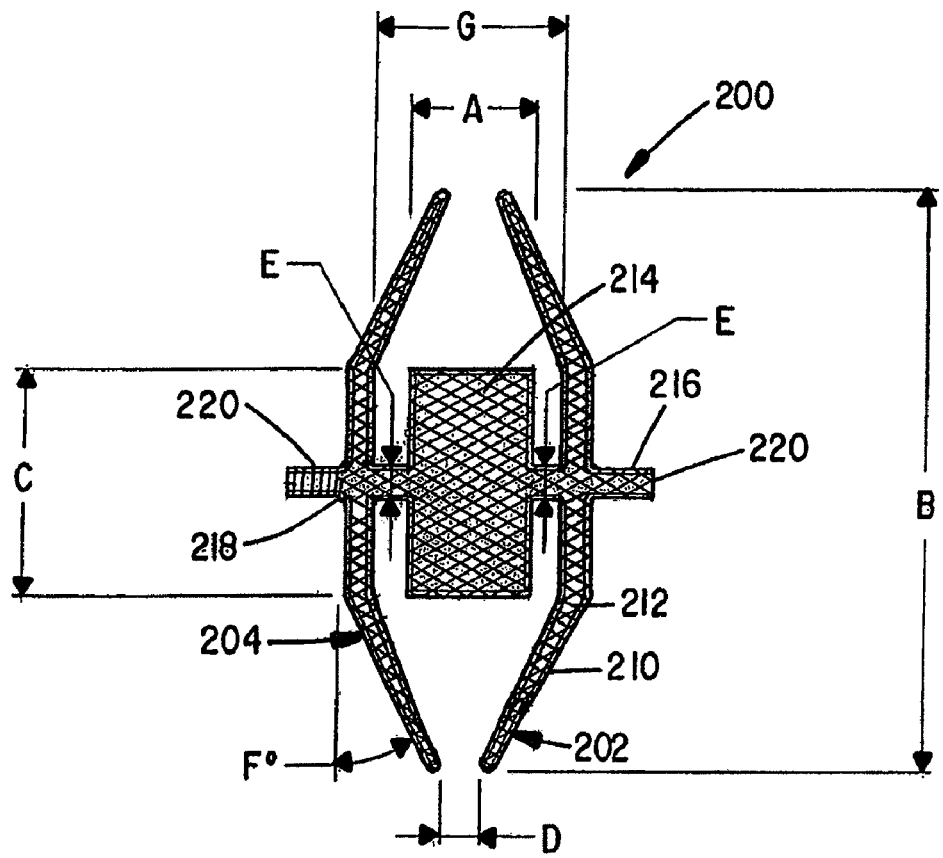
Figure 11B:
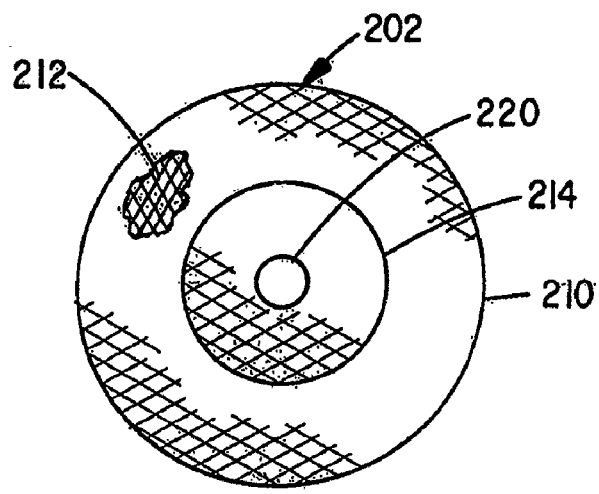

An alternative embodiment of a device 200 for the treatment of a PDA is shown is FIGS. 11a-11d. The device 200 in its relaxed, unstretched state has two disks 202 and 204 aligned in spaced relation, linked together by a cylindrical segment 214 (i.e., six planes of occlusion). The length of the cylindrical segment 214 may approximate the thickness of the atrial septum. The proximal 202 and distal 204 disks may have an outer diameter sufficiently larger than the cavity, opening, or the like to prevent dislodgement of the device. The disks 202 and 204 are generally frustroconical in configuration, with the larger diameter portions facing one another. Thus, as shown in FIG. 11a, the disks 202 and 204 taper from a smaller diameter C to a larger diameter B. The angle F extending between diameters B and C may vary and may be, for example, between about 20 and 40 degrees. Similarly, the distance between the smaller and larger diameter surfaces of each disk 202 and 204 may vary. The disks 202 and 204 are configured to extend inwardly to slightly overlap the cylindrical segment 214, which can be seen in the cross-sectional view of FIG. 11a. As also shown in FIG. 11a, the cylindrical segment 214 connects with each of the disks 202 and 204 at a diameter E which is smaller than both the diameter of the cylindrical segment and the disks. This configuration may allow the disks 202 and 204 to easily pivot about diameters E to allow the disks to align themselves with anatomical vessel walls that are not perpendicular to the aperture therebetween. Although the device 200 may have one or more layers of occlusive material, FIG. 11a shows that the device may include an inner layer 212 and an outer layer 210. As noted above, the ends 216 and 218 of the braided layers may be secured with clamps 220 in order to prevent the braids from unraveling.

Figure 11F:
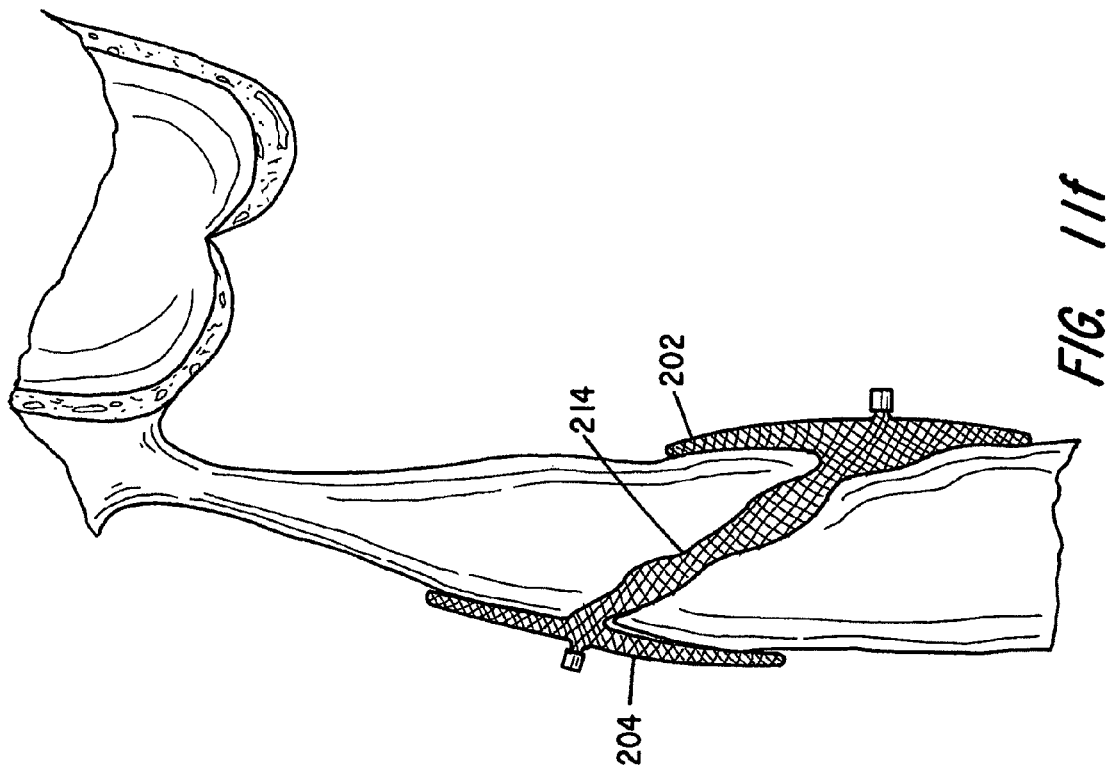
Figure 11E:
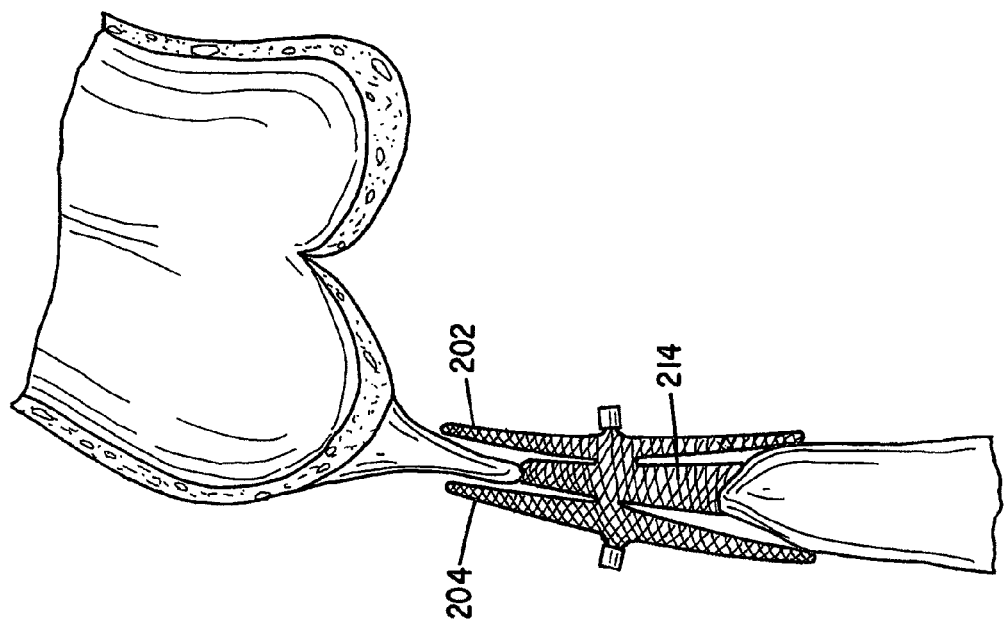

FIG. 11c illustrates a condition where the disks 202, 204 are relatively parallel but at a substantial angle to the central section or device axis. The central section is elongated due to a smaller passage than anticipated and the elongation accommodates the lengthened passage between disks. In FIG. 11d the disks are non-parallel to accommodate the walls of the aorta and again the central section is elongated as it conforms to the passageway between the disks. FIG. 11e illustrates a device placed in a para-membranous VSD. In this case the device is shown conforming to a thin membrane at the upper portion of the defect and to the thicker septum in the bottom portion of the defect. The central section fully expands to shorten the distance between disks to aid in clamping force and to fill the defect. FIG. 11f shows a device placed in a tear through a ventricular septum. The device central section 214 elongates to fill the tear and the disks conform to the septum walls.

The device 200 is symmetrical so that is may be deliverable by catheter venously or arterially, such as from either the pulmonary side or the aortic side as selected by the physician. The advantage of a venous approach for PDA closure is to potentially treat infants as small a 1 kg. The advantage of an arterial approach in slightly larger premature infants is that both angiography and device implant can take place from a common access point in the femoral artery.

The device 200 may have various dimensions depending on the particular vessel or abnormality to be occluded. For example, the cylindrical portion 214 of diameter C may range from 2 mm to 6 mm. The length of the cylindrical central section A, may range from 2 mm to 8 mm. The reduced diameter E may range from 1 mm to 2 mm, preferably 1 mm (or a tightly bunched group of wires). The ratio of the large disk diameter B to the small diameter E may range from 6 to 12 mm. This ratio may allow the disks to conform or pivot to a wide range of wall angles relative to the axis of the PDA, which in the four exemplary examples of FIG. 11c-11f. In addition, the disks may be spaced apart at their outermost point a distance D that ranges from 1 mm to 3 mm. The distance between the inner surface of each disk, in the portion (C) perpendicular to the device central axis, is G and may range from 3 to 7 mm. The difference between distance G and A may provide for passageway length variability and conformability to surface irregularities as well as act like a spring to apply clamping pressure at each disk to the vessel to hold the device in place. Diameter C may be selected to be slightly larger (e.g., 10-20%) than the passageway it is intended for in order to facilitate anchoring of the device. If the passageway is longer than anticipated, the central portion can elongate to accommodate the longer length.

Figure 12A:
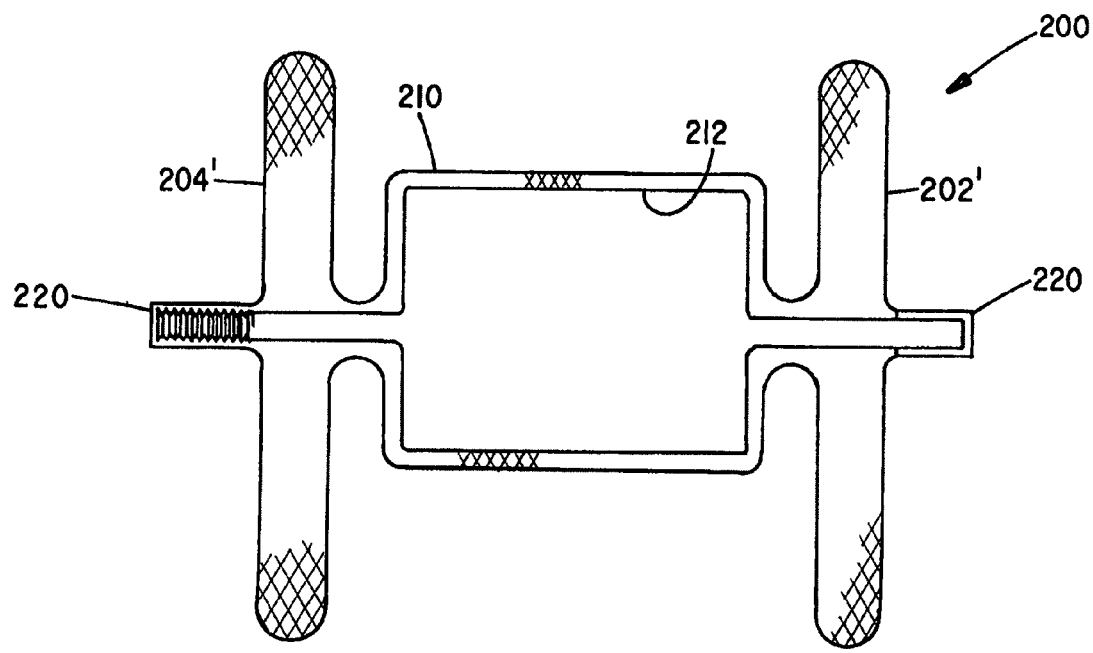
FIGS. 12a-12f show variations of occluder devices according to additional embodiments of the present invention.
Figure 12B:
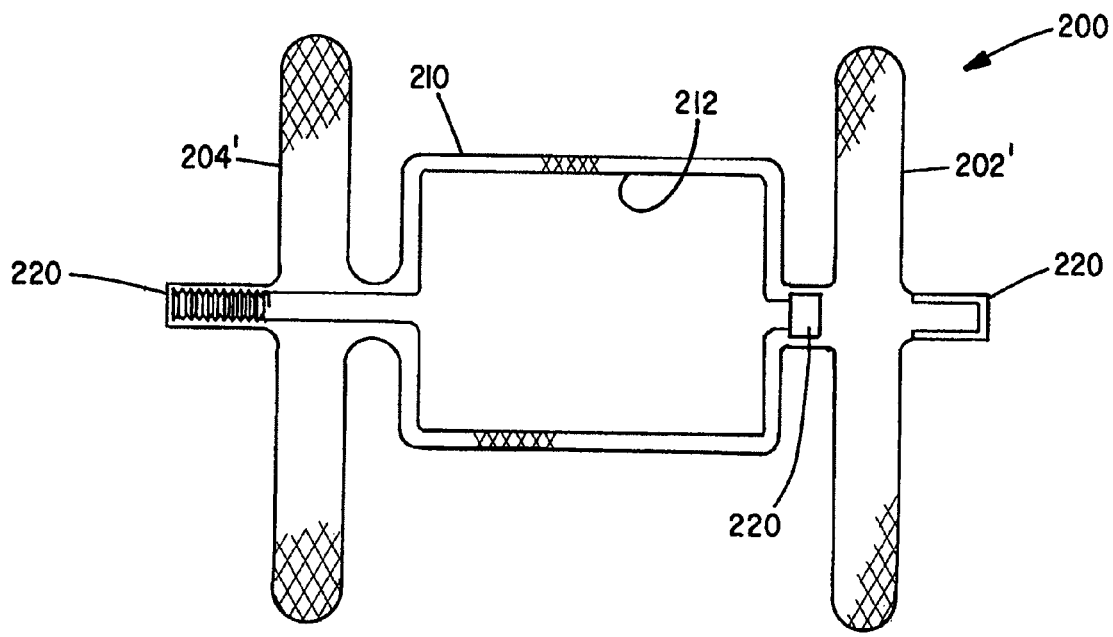
Figure 12C:
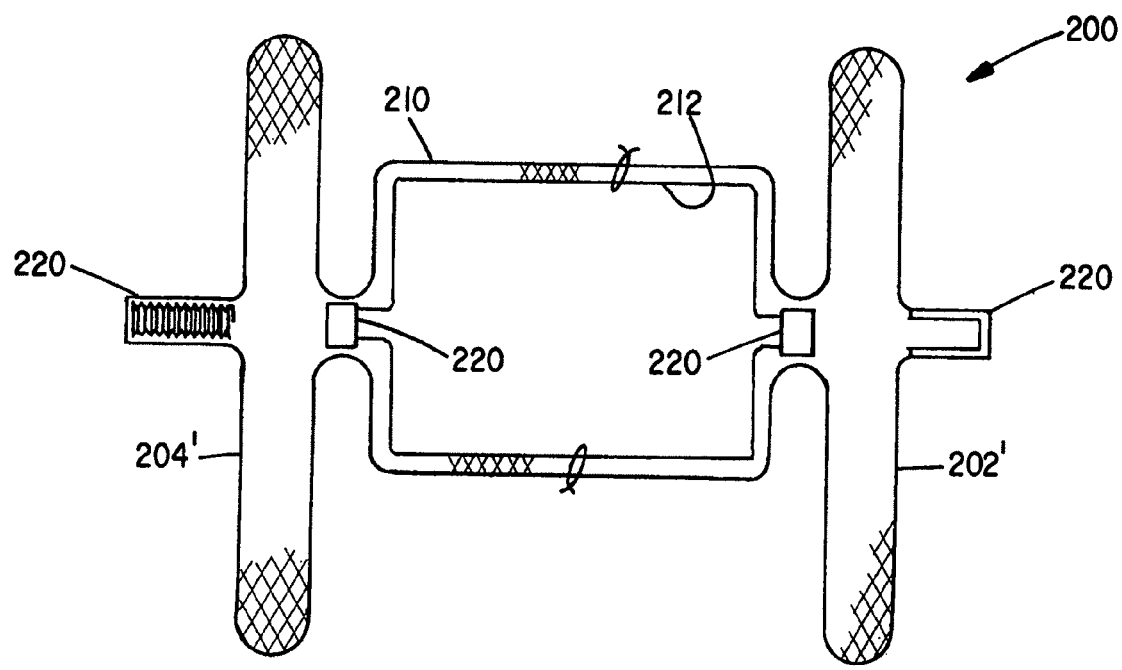
Figure 12D:
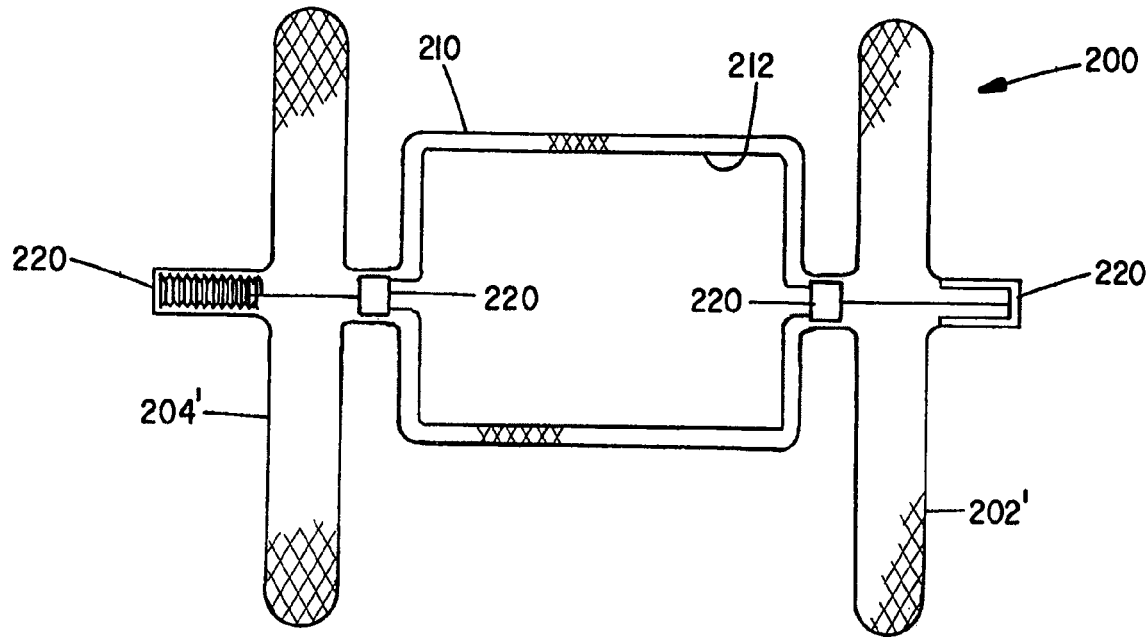
Figure 12E:
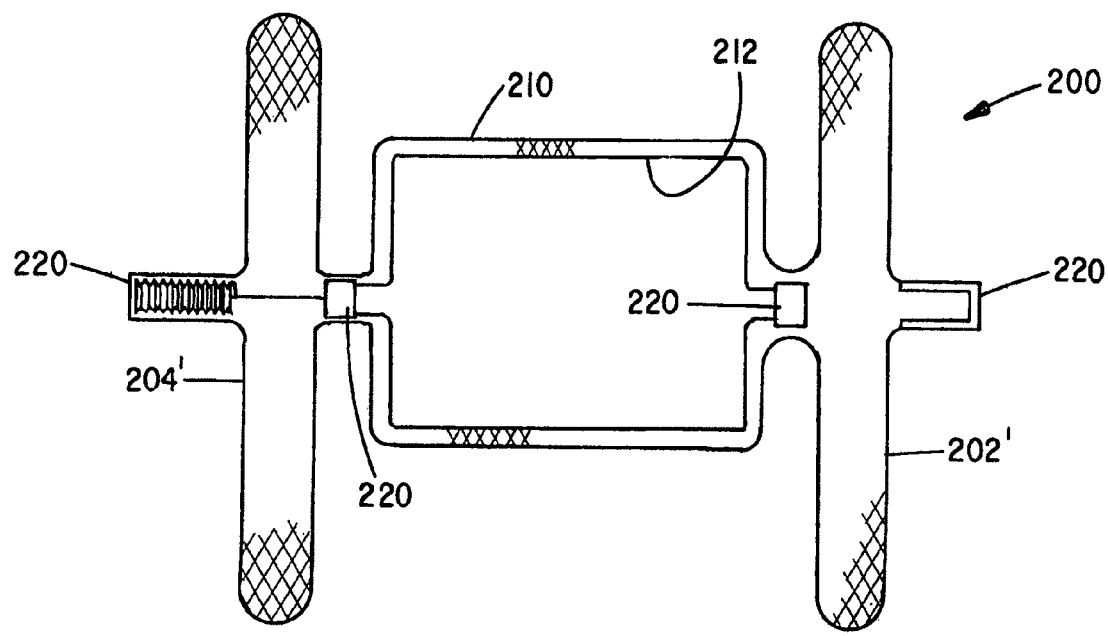
Figure 12F:
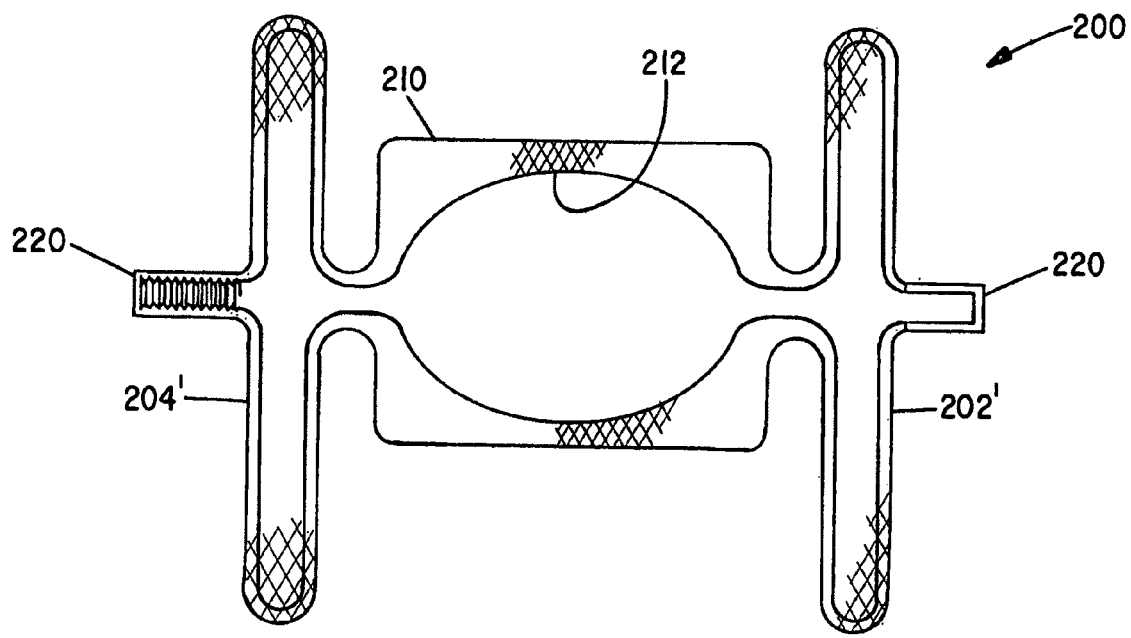

Other alternative embodiments of the present invention are shown in FIGS. 12a-12f. In FIG. 12a the disks 202' and 204' are fabricated from a single layer folded back on itself, while the central portion is double layered. FIG. 12f shows an embodiment where the design is reversed to have double layers in the disk portion back to back, with a single layer in the central portion or a different shape for each layer in the central portion as shown. FIG. 12b illustrates a design variation where the multiple braid layers have end wires connected at one end in a common clamp 220 but where the inner layer at the opposite end has a clamp 220 that free floats and is separate from the clamp for the outer layer. In the embodiment of FIG. 12c the inner layer 212 is suspended by suture connectors between the layers and the end clamps of each layer are independent of each other. In FIG. 12d the inner layer 212 has independent end clamps 220 as in FIG. 12c, but rather than the layers connected by sutures, the layers 210 and 212 have their end clamps connected by elastic members, such as made from silicone rubber. FIG. 12e is similar to FIG. 12d except that the connector could be a non-elastomer such as suture or wire and may be connected optionally at only one set of end clamps. Like the embodiments of FIGS. 11a-11f, the embodiments shown in FIGS. 12a-12f have a small transition diameter extending between each disk 202' and 204' and the central portion. It is anticipated that the various optional characteristics, as shown in FIGS. 12a-12f, could be combined in any manner desired for any embodiment described herein.

Figure 13A:
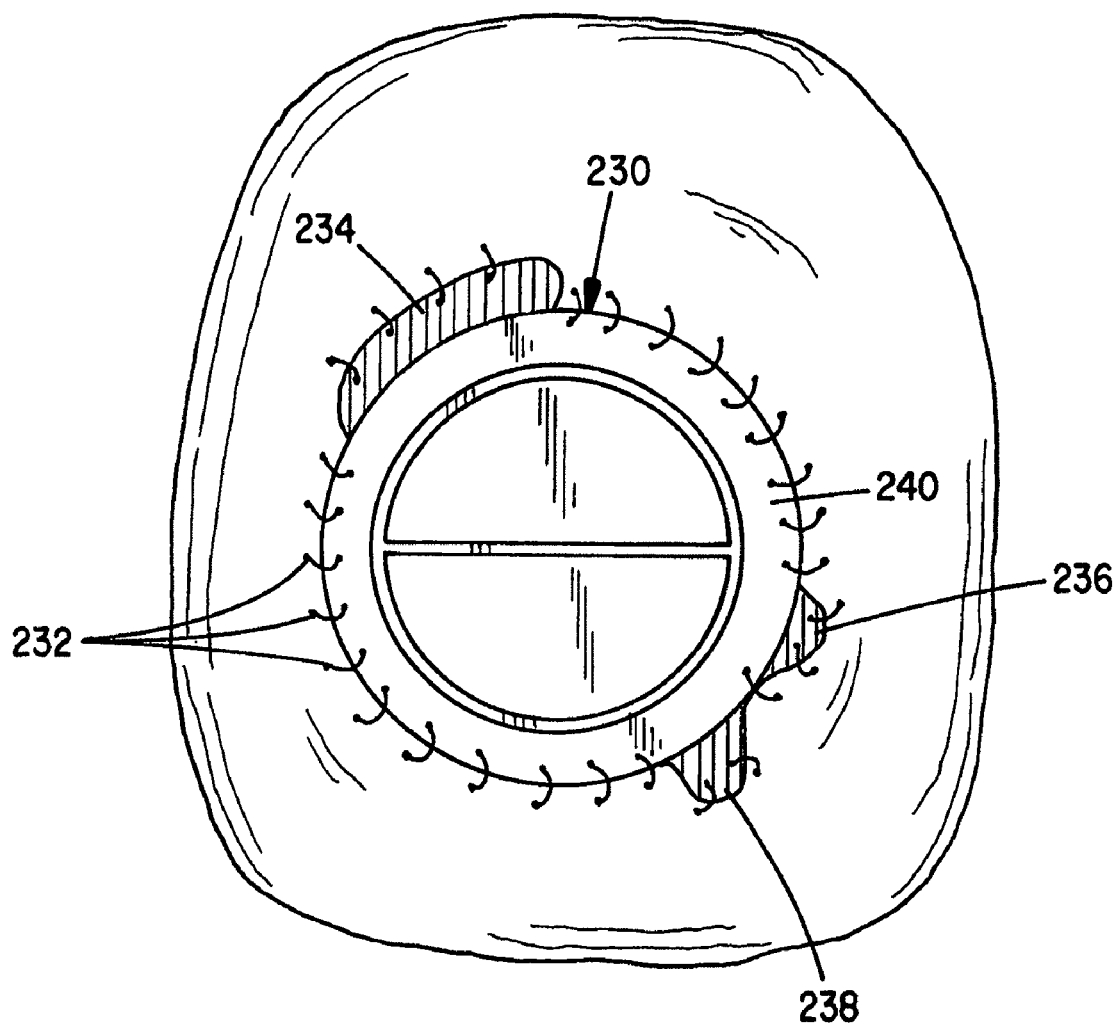
FIG. 13a is an example of a PVL anatomy.

Various embodiments for treating vascular abnormalities, such as PVLs and PDAs, are illustrated in FIGS. 13a-13h. FIG. 13a shows an artificial bi-leaflet valve 230 sewn by suture 232 into a patient. Three cross-hatched areas 234, 236, and 238 along the valve cuff represent open areas where tissue has pulled away from the cuff from weak tissue or broken or loose sutures. These open areas allow blood to short circuit the valve and result in poor heart function and lower blood pressure. As shown in FIGS. 13b-13e, various devices are configured to close/occlude these PVLs such as are shown in FIG. 13a.

With reference to FIG. 13b-I, the outer layer 310 of the device 300 includes a frame that defines the outer shape of the medical device 300. Within this frame is an inner layer 312. The device 300 may further include a third layer 314 (not shown) as an innermost liner. As noted above, the ends 316 and 318 of the braided layers may be secured with clamps 320 in order to prevent the braids from unraveling.

Figure 13B:
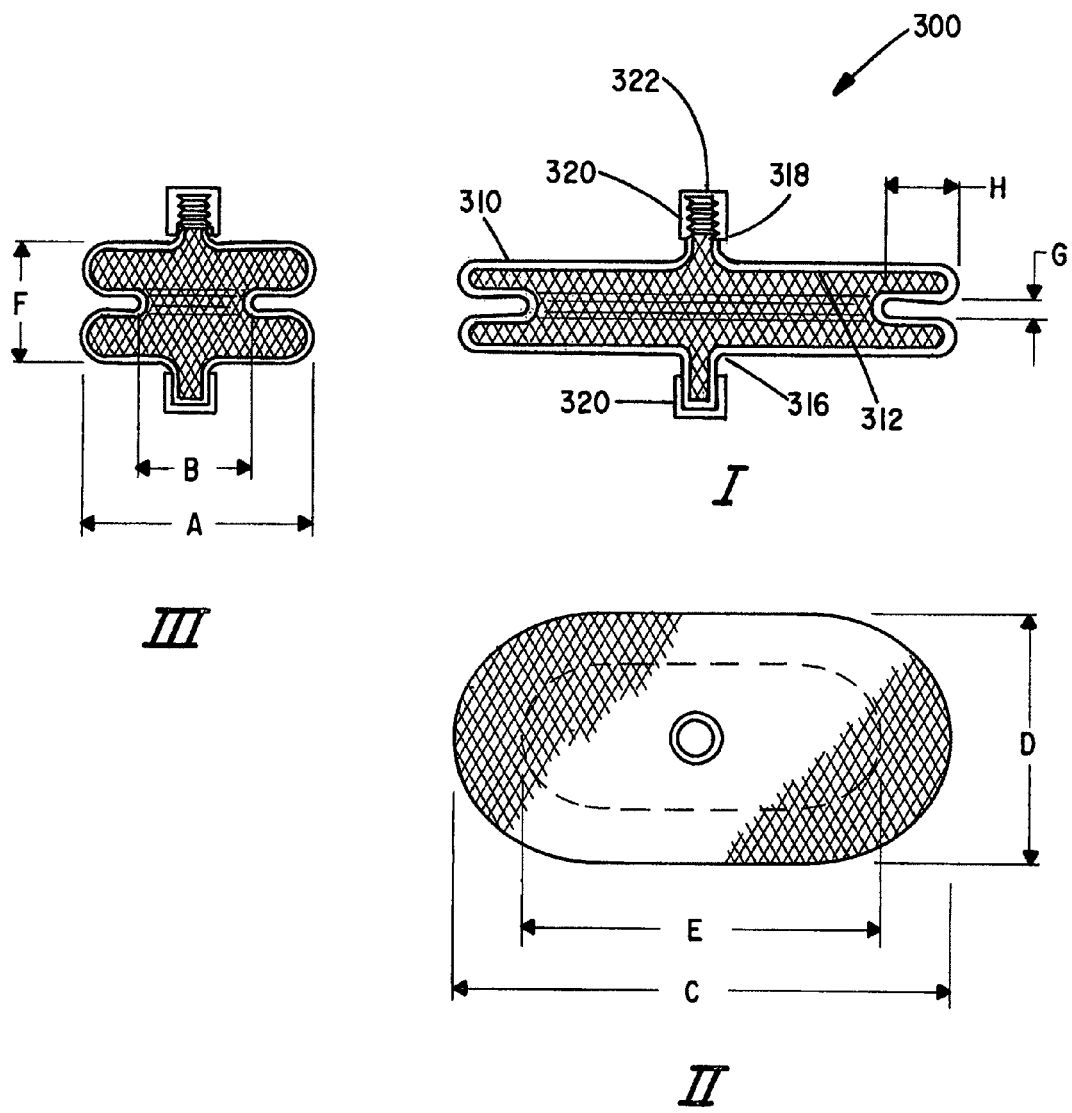
FIGS. 13b-h illustrate various occluder devices for treating vascular abnormalities according to various embodiments of the present invention.
Figure 13D:
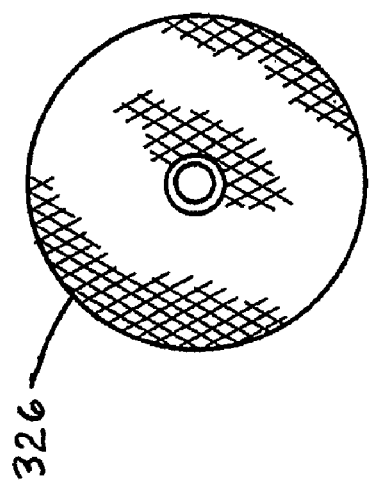
Figure 13C:
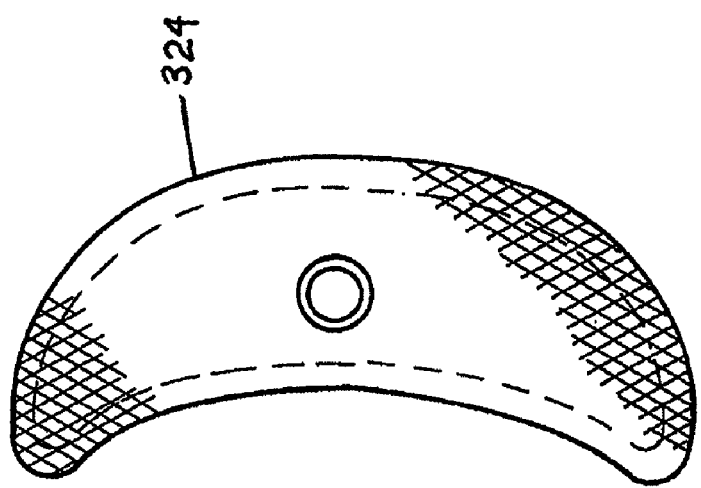
Figure 13E:
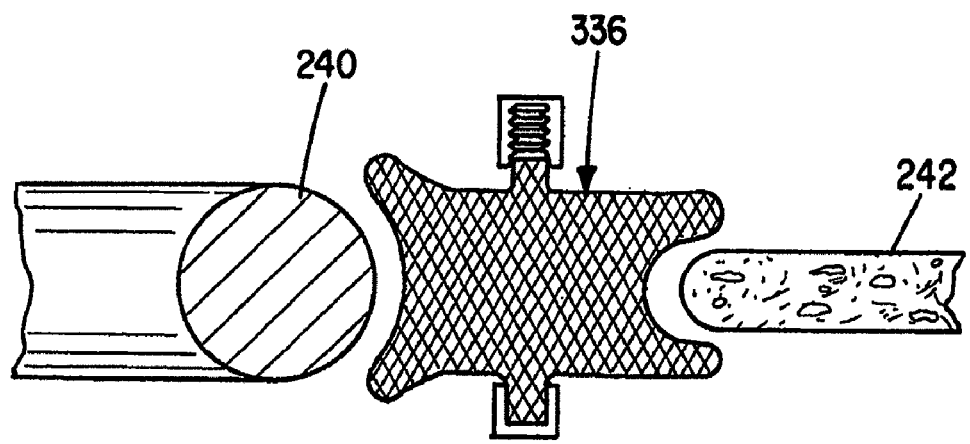

Since the openings of the vascular abnormalities may be of various shapes it is anticipated that a number of sizes and shapes of occluder devices may be needed to close these leaks. It is also important that the occluder be positioned securely to prevent migration or embolization of the device. As shown in FIG. 13b-I, device 300 is formed of two layers each having the same shape. FIG. 13b-II is a plan view of device 300 and FIG. 13b-III is an end view thereof. This particular design is intended to occlude openings that are somewhat oblong in shape. Radiopaque markers may be placed either on the narrow or wide side of the expanded shape to help the physician orient the device as needed. These markers may be radiopaque platinum wire or platinum iridium markers attached to the braid in a manner which does not impede braid collapse or self expansion. Since the wire diameter is small, the oblong shape of the device 300 shown in FIG. 13b may conform to shapes that may be more rounded or longer. FIG. 13c illustrates a crescent-shaped occluder 324, and FIG. 13d illustrates a round occluder 326. The inside radius of the crescent-shaped occluder 324 may be about 11°, and the occluder may incorporate a radiopaque marker to facilitate proper orientation thereof. The crescent-shaped occluder 324 may be useful in areas such as around valves. In FIG. 13e, one edge of the device 336 that interfaces with the cuff 240 is shaped to match the cuff shape whereas the other side that interfaces with the tissue 242 has a shape more conducive to the thickness of the tissue at the interface.

Figure 13F:
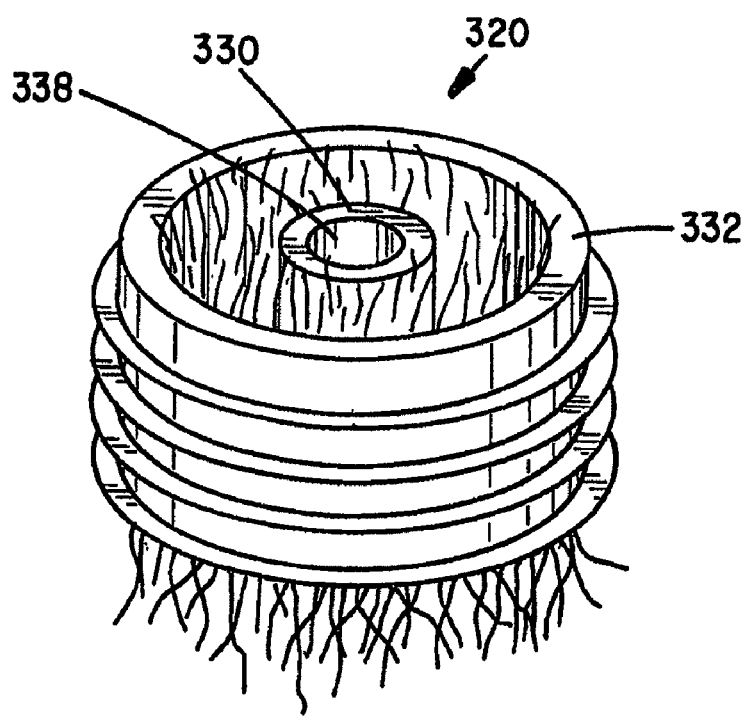
Figure 13G:
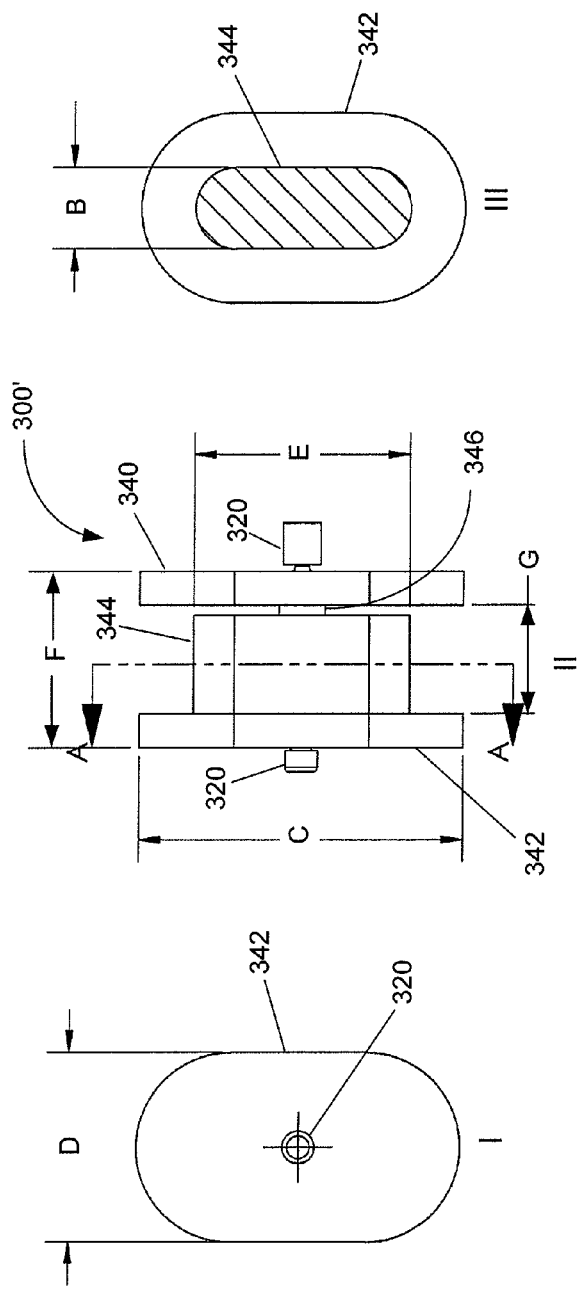
Figure 13H:
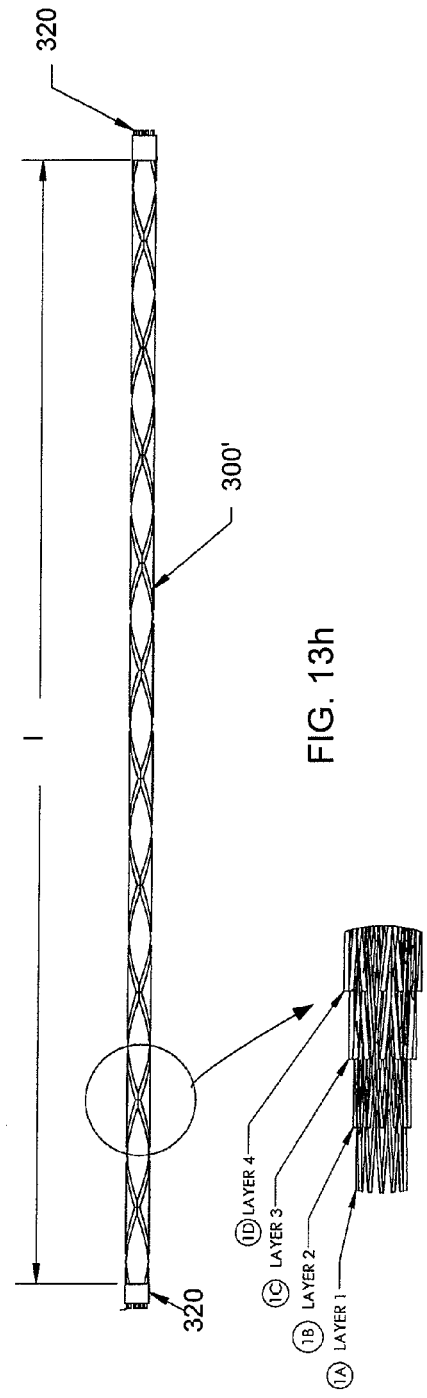

Furthermore, FIG. 13g illustrates an additional embodiment of an oblong or oval-shaped occluder 300'. In this particular embodiment, the device 300' includes a pair of oval disks 340, 342 and a portion 344 that is also oval in configuration. Extending between the disk 340 and the oval portion 344 is a narrow waist 346 to facilitate articulation therebetween. At the opposite side of the device 300', the disk 342 necks down to the oval portion 344. It is understood that there may also or alternatively be a narrow waist 346 extending between the disk 342 and the oval portion 344 according to additional aspects of the present invention. Furthermore, FIG. 13h illustrates that device 300' in an elongated state, wherein the device may be elongated for delivery within a delivery device. FIG. 13h also illustrates that the device 300' comprises four layers of fabric that are heat set to self expand from an elongated configuration to the unconstrained configuration shown in FIG. 13g. Thus, the device shown in FIG. 13h may have at least 5 planes of occlusions (i.e., 2 for disk 340 (opposing surfaces of the disk), 2 for disk 342 (surfaces adjacent and opposite the oval portion 344), and 1 for the oval portion 344 (surface coupled to the waist 346). For illustrative purposes, dimensions are given for the oblong occluders of FIGS. 13b and 13g in Tables 1 and 2, as well as dimensions for exemplary delivery catheters for delivering such devices. As shown in Table 2, the oblong occluders may have two to four layers of occlusive fabric material. The dimensions of each Braid Layer in Table 2 correspond to the strand diameter, number of strands, and the diameter of the mandrel on which the strands were braided.

TABLE 1

| Waist (E × B mm) | Device Length (F mm) | Sheath Minimum | Minimum ID (in.) | Guide Catheter Minimum | C (mm) | D (mm) | I (mm) | G (mm) |
| --- | --- | --- | --- | --- | --- | --- | --- | --- |
| 4 × 2 | 6.5 | 5F | 0.066 | 6F | 8.0 | 6.0 | 21.0 | 4.0 |
| 6 × 3 | 6.5 | 5F | 0.066 | 6F | 10.0 | 7.0 | 25.25 | 4.0 |
| 8 × 4 | 6.5 | 5F | 0.074 | 7F | 12.0 | 8.0 | 29.5 | 4.0 |
| 10 × 5 | 6.5 | 6F | 0.070 | 8F | 14.0 | 9.0 | 33.0 | 4.0 |
| 12 × 5 | 6.5 | 6F | 0.070 | 8F | 16.0 | 9.0 | 36.5 | 4.0 |
| 14 × 5 | 6.5 | 7F | 0.070 | 9F | 18.0 | 9.0 | 44.0 | 4.0 |

TABLE 2

| Device Size (mm) | Braid Layer A | Braid Layer B | Braid Layer C | Braid Layer D |
| --- | --- | --- | --- | --- |
| 4 × 2 | 0.0015 × 144 × 8 mm | 0.0015 × 144 × 8 mm | N/A | N/A |
| 6 × 3 | 0.0015 × 144 × 12 mm | 0.0015 × 144 × 12 mm | 0.0015 × 144 × 12 mm | N/A |
| 8 × 4 | 0.0015 × 144 × 12 mm | 0.0015 × 144 × 12 mm | 0.002 × 144 × 12 mm | N/A |
| 10 × 5 | 0.0015 × 144 × 15 mm | 0.0015 × 144 × 15 mm | 0.002 × 144 × 15 mm | N/A |
| 12 × 5 | 0.0015 × 144 × 17 mm | 0.0015 × 144 × 17 mm | 0.002 × 144 × 17 mm | 0.002 × 144 × 17 mm |
| 14 × 5 | 0.0015 × 144 × 20 mm | 0.0015 × 144 × 20 mm | 0.002 × 144 × 20 mm | 0.002 × 144 × 20 mm |

FIG. 13f illustrates an exemplary clamp 320 for the device 300 intended to be compatible with delivery of the occluder over a guidewire. In this design the clamps 320 have a central passage 338 for the guidewire to slidable pass there through. The clamp 320 is therefore fabricated with an inner ring 330 having an inside diameter slightly larger (e.g., about 0.002-0.004 inch) larger than the guidewire diameter. The clamp also has an outer ring 332 large enough to contain the braided wire ends between the two rings. The outer ring 332 may be swaged to compress the outer ring against the wires and the inner ring 330 or the wire ends and rings may be welded, brazed, soldered or held by adhesive or other known techniques. At least one of the clamps may have threads either externally on the outer ring of the clamp or internally in the inner ring to accommodate a threaded delivery device having an internal lumen sized for passage of a guide wire therethrough.

Figure 14A:
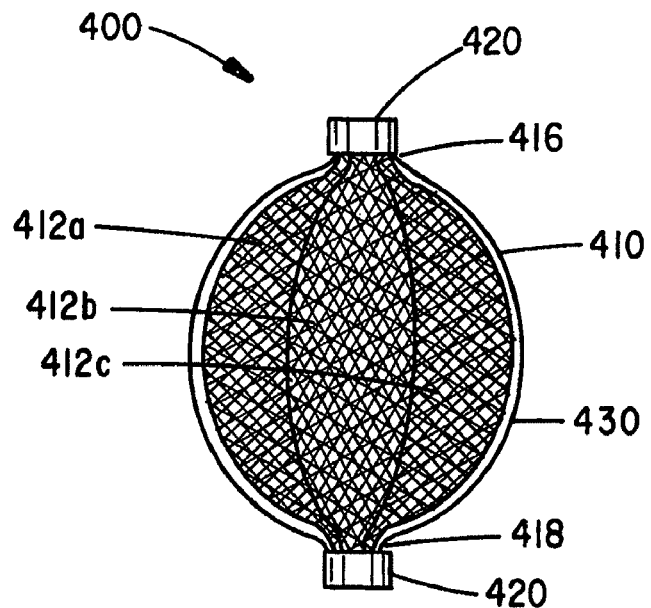
FIGS. 14a-14c are views of an occluder device according to a further embodiment of the present invention.
Figure 14B:
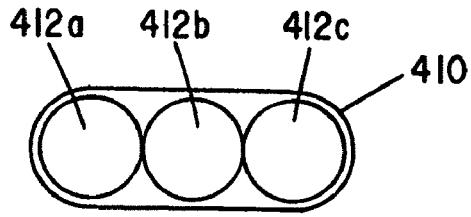
Figure 14C:
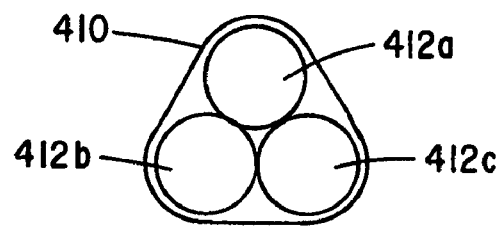

Another embodiment of an occluder is a variation of the devices shown in FIGS. 12a-12f, whereby the occluder device 400, as shown in FIGS. 14a-14c, includes a soft, conformable, outer braid 410 enclosing a volume 430 that is pre-shaped as desired, with two or more internal braided tubular members 412a, b, c side by side with shared braid end wire connectors 420 at least at one end. As can be seen in FIGS. 14b and 14c, the multiple braids need not be concentric. This arrangement allows the inner braided members 412 to shift relative to one another to fill the available volume of unknown size or shape such as an oblong, crescent, or oval cavity shape. This is accomplished by selecting a heat set shape for braids 412 that have a large enough diameter to exert a force against the outer tubular braid 410 to compel the outer braid against the wall of the cavity the device is placed in. To share a common end wire clamp 420 the internal braided members 412 may be clamped with end clamps 420, such as by compressing the braided members against each other at the ends and shaped into a crescent to fit in annular fashion about the end clamp 420. The proximal clamp 420 at wire end 418 may have threads (not shown) for connection to a delivery catheter (not shown). The proximal wire ends of braids 412 be connected to clamp 420 by means of a tether or elastic member to allow for a braid length change that would vary based on the shape of the device 400 within a cavity. In addition, an optional over the guidewire delivery embodiment may be employed as described in previous embodiments.

Figure 15:
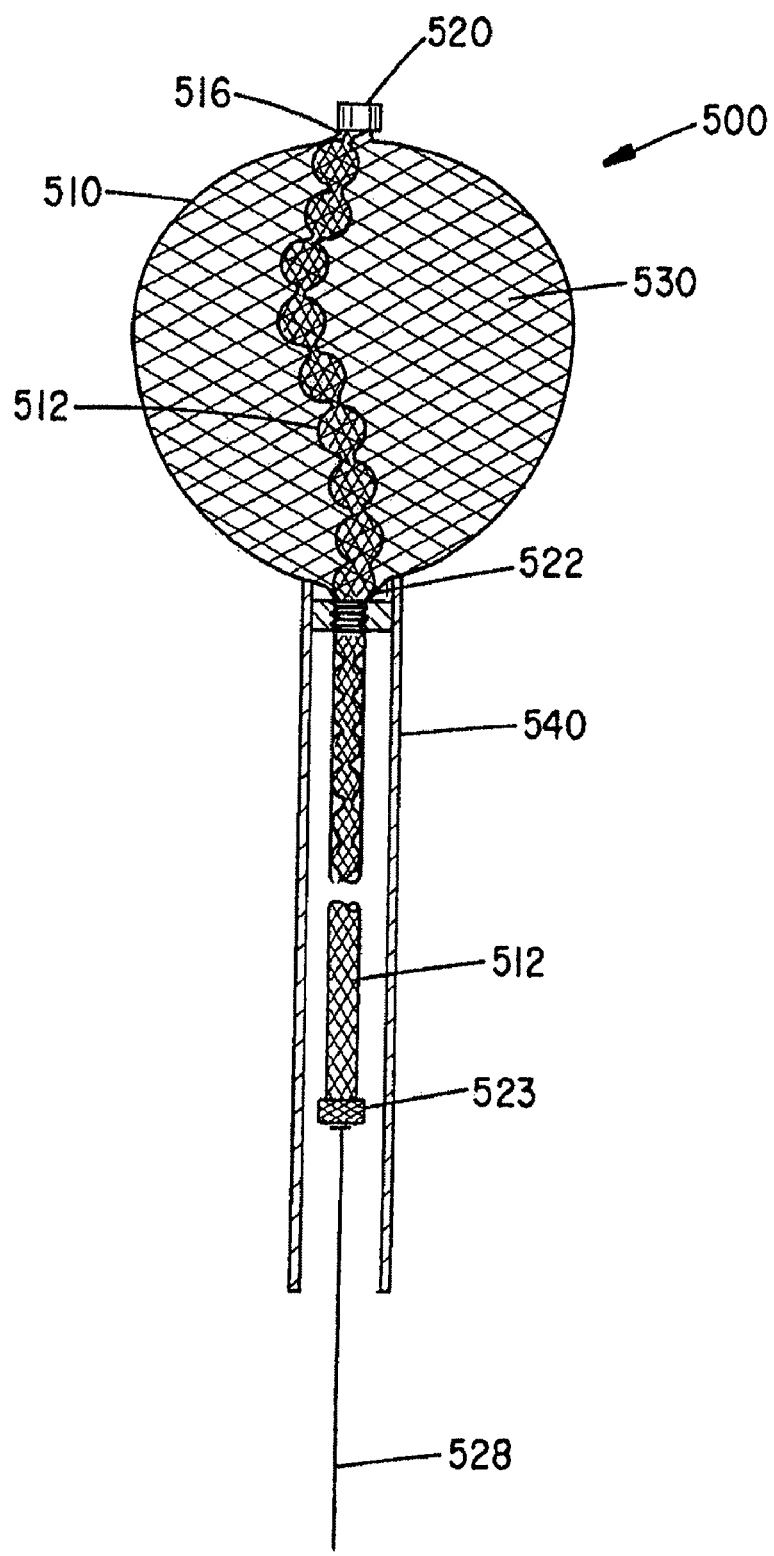
FIG. 15 depicts an embodiment of an occluder device wherein an inner braid fills an outer braid volume.

In a further embodiment of a device 500 shown in FIG. 15, the outer braid 510 may be pre-shaped to define a volume shape 530 that is soft and conformable. Contained within the outer braid and coaxially sharing the outer braid distal wire end clamp 520 is a smaller diameter tubular braid 512 that is pre-shaped into a bead and chain shape. The internal smaller braid 512 is much longer than the outer braid 510 and is designed to meander into the outer braid defined volume 530 as braid 512 is inserted to fill the volume completely and help the outer braid to conform to the cavity shape it is within. The distal braided wire end clamp 520 at wire end 516 is preferably a two part clamp arrangement with an internal ring and external ring pinching the braid wires between the rings. The proximal braided wire end clamp 522 is similarly constructed but the outer ring is threaded to mate with threads on the delivery catheter 540 for selective connection between the device and the delivery catheter. In this embodiment, a portion of the inner braid remains within the delivery catheter when the outer braid is fully deployed. In order to deliver the balance of the inner tubular braid 512 into the volume 530, a pusher wire 528 within the delivery catheter 540 acts against the proximal end wire end clamp 523 of braid 512 to advance the braid completely out of the delivery catheter. The pusher wire 528 may optionally have a threaded end to engage with optional threads in the wire end clamp 523. The delivery catheter 540 may be advanced to the treatment site through a sheath. The high density of wire within the volume 530 may facilitate rapid hemostasis while maintaining a low profile for delivery. The spherical shape of the bead chain fills the volume with sphere against sphere against the outer braid and thereby loads the outer braid surface against the cavity wall desired to be occluded. The wire end clamps 520 and 523 may be of the two ring configuration as previously described in other embodiments to allow the device to be configured for over the guidewire delivery.

Figure 16A:
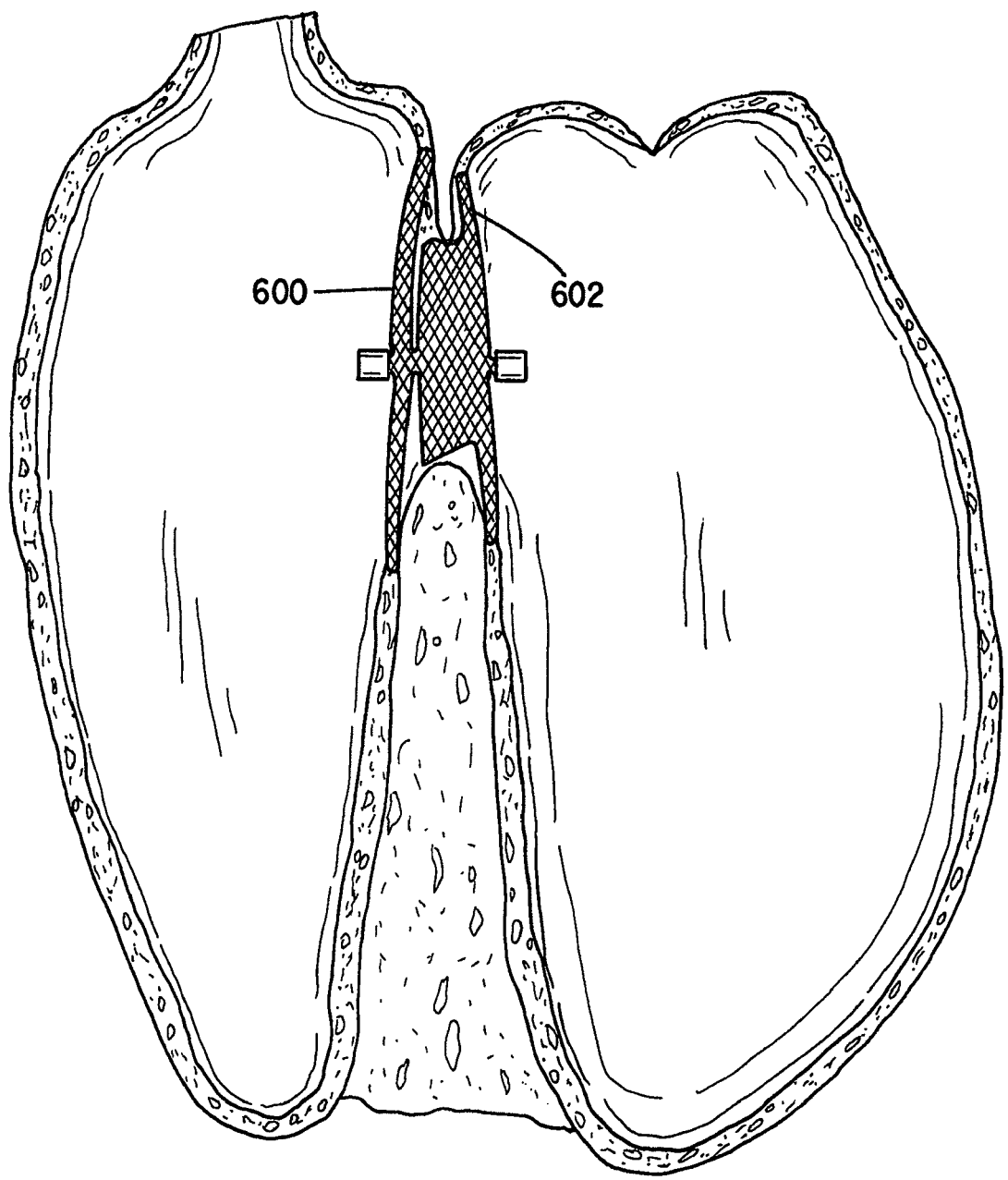
FIGS. 16a-16d are views of an occluder device according to alternative embodiments of the present invention.
Figure 16B:
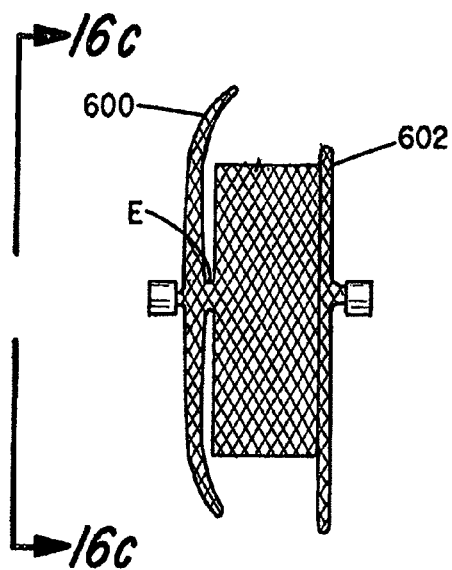
Figure 16D:
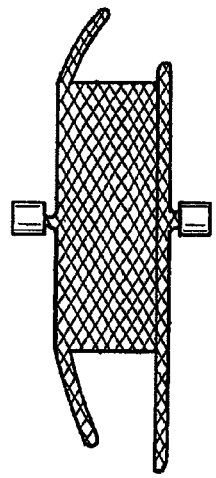
Figure 16C:
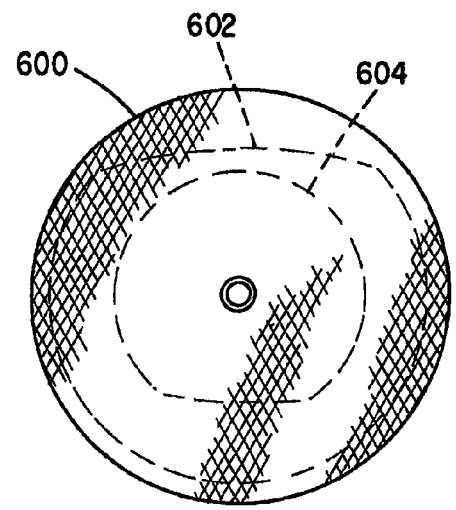

In another embodiment as shown in FIGS. 16a-16d, intended primarily for para-membranous VSD occlusion. The device may have one articulating flange 600 (right chamber) with a small transition diameter E, and the flange 602 on the opposing end (left chamber) may be smaller in diameter to prevent interference with the aortic valve. The single articulating flange 600 may reduce pressure of the conductive His bundle to help prevent heart block, and the lack of articulation on the left chamber side may better resist dislodgement of the device from the higher arterial blood pressure (FIGS. 16b and 16c). In order to relieve the left chamber flange 602 diameter to prevent interference with the aortic valve, the left chamber flange may be offset from the central axis with respect to the central device portion so that the flange is displaced away from the valve as shown in FIG. 16d. Further modification, by eliminating transition diameter E is also anticipated as shown in FIG. 16d.

The embodiments described above may be employed for treating various vascular abnormalities, such as PDA, VSD, ASD, PFO, PVL, or any other similar abnormality. The various occluder embodiments described above may occlude relatively quickly compared to prior art devices due the increased number of occlusion planes, as well as the small pore size and large surface area created by the multitude of wires resulting from using multiple layers of occlusive material. Because of the increase in the number of wire strands in a composite multi-layer structure, it may no longer be necessary to incorporate a sewn-in polyester material in order to reduce the time required to establish total occlusion of a PDA, VSD, ASD, PFO, PVL, or other vascular location. In addition, the occluder devices may have a lower profile, improved retention force, and improved conformability to adjust to a variety of vessel passageways with minimal interference in the native vessel flow. The reduced profile of this device may be configured for delivery within a 4 French catheter or sheath. Over the guidewire tracking offers options for delivery to difficult to reach anatomy. Due to device symmetry, some embodiments are deliverable from either the venous or arterial side of the same defect.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A medical device for occluding an abnormality, the medical device comprising:
an expanded preset configuration having proximal and distal ends, the expanded preset configuration comprising a disk at each of the proximal and distal ends and a central portion disposed between the disks, each of the disks and the central portion disposed along a central axis extending between the proximal and distal ends, wherein each of the disks comprises a plurality of planes of occlusion and the central portion comprises at least one central plane of occlusion, at least one of the planes of occlusion of the disks or the central portion comprising a plurality of separate layers of braided metal fabric, wherein each of the planes of occlusion of the disks and the central portion is oriented generally transverse to the central axis and is configured to be oriented generally transverse to blood flow such that the layers of braided metal fabric are configured to substantially occlude blood flow therethrough so as to occlude the abnormality in less than about 10 minutes, and wherein at least one of the plurality of planes of occlusion at the proximal or distal ends has a larger cross-sectional area than the at least one central plane of occlusion in the expanded preset configuration.

2. The medical device of claim 1, wherein the medical device is configured to substantially occlude the abnormality in less than about 5 minutes.

3. The medical device of claim 1, wherein the medical device is configured to substantially occlude the abnormality in less than about 3 minutes.

4. The medical device of claim 1, wherein the medical device comprises at least five planes of occlusion.

5. The medical device of claim 1, wherein at least one of the plurality of planes of occlusion comprises at least three layers of braided metal fabric.

6. The medical device of claim 1, wherein at least one of the plurality of planes of occlusion at the proximal or distal ends is configured to overlie an opening of the abnormality.

7. The medical device of claim 1, wherein the at least one central plane of occlusion is configured to be at least partially positioned within an opening defined by the abnormality.

8. The medical device according to claim 1, wherein at least one of the plurality of planes of occlusion of the disks or the at least one central plane of occlusion is oval or crescent shaped in cross section.

9. The medical device according to claim 1, wherein at least one of the plurality of planes of occlusion of the disks or the at least one central plane of occlusion is non-circular in shape in cross section.

10. The medical device of claim 1, wherein the medical device is configured for delivery over a guide wire.

11. The medical device of claim 1, wherein at least one of the disks at the proximal or distal ends is configured to articulate about the central portion.

12. The medical device of claim 11, further comprising a waist extending between one of the plurality of planes of occlusion at the proximal or distal end and the at least one central plane of occlusion, the waist having a smaller cross-sectional area than both the one of the plurality of planes of occlusion at the proximal or distal end and the at least one central plane of occlusion, and wherein the one of the plurality of planes of occlusion at the proximal or distal ends is configured to articulate with respect to the at least one central plane of occlusion about the waist.

13. The medical device of claim 1, wherein each of the disks at the proximal and distal ends and the central portion has an oval-shaped cross section.

14. The medical device of claim 1, wherein the plurality of layers of braided metal fabric extend substantially between the proximal and distal ends.

15. The medical device of claim 14, wherein each of the plurality of layers of braided metal fabric comprises a tubular member.

16. The medical device of claim 14, wherein the plurality of layers of braided metal fabric are disposed concentrically to one another.

17. The medical device of claim 1, wherein the expanded preset configuration is deformable to a lesser cross-sectional dimension for delivery to the abnormality, at least one of the plurality of layers of braided metal fabric having a memory property such that the medical device tends to self expand and return to the expanded preset configuration when unconstrained.

18. The medical device of claim 1, wherein each of the plurality of planes of occlusion at the proximal and distal ends and the central plane of occlusion is oriented generally transverse and coaxial to the central axis.

19. The medical device of claim 1, wherein at least one of the layers of braided metal fabric comprises Nitinol.

20. A method for occluding an abnormality with a medical device, the method comprising:
constraining the medical device of claim 1 to a smaller diameter than the expanded preset configuration;
delivering the medical device proximate to the abnormality; and
deploying the medical device proximate to the abnormality such that the plurality of planes of occlusion and the at least one central plane of occlusion are oriented generally transverse to blood flow and such that the layers of braided metal fabric substantially occlude blood flow therethrough so as to occlude the abnormality.

21. The method of claim 20, wherein constraining comprises stretching the medical device along a longitudinal axis thereof to the smaller diameter.

22. The method of claim 20, wherein deploying comprises deploying the medical device such that at least one of the plurality of planes of occlusion at the proximal or distal ends is configured to overlie an opening of the abnormality.

23. The medical device of claim 20, wherein deploying comprises deploying the medical device such that the at least one central plane of occlusion is at least partially positioned within an opening defined by the abnormality.

24. The method of claim 20, wherein delivering comprises delivering the medical device over a guide wire.

25. The method of claim 20, wherein delivering comprises delivering the device arterially or venously proximate to the abnormality.

26. A medical device for occluding an abnormality comprising:
an expanded preset configuration having proximal and distal ends, the expanded preset configuration comprising a disk at each of the proximal and distal ends and a central portion disposed between the disks, each of the disks and the central portion disposed along a central axis extending between the proximal and distal ends,
wherein each of the disks comprises a plurality of planes of occlusion and the central portion comprises at least one central plane of occlusion, wherein each of the planes of occlusion of the disks and the central portion is oriented generally transverse to the central axis and is configured to be oriented generally transverse to blood flow, at least one of the planes of occlusion of the disks or the central portion comprising a plurality of separate layers of braided metal fabric, wherein at least one of the plurality of planes of occlusion at the proximal or distal end is configured to be positioned within a vessel or an organ and overlie an opening of the abnormality, and wherein the at least one central plane of occlusion is configured to be at least partially positioned within the opening defined by the abnormality such that the layers of braided fabric are configured to substantially occlude blood flow therethrough so as to occlude the opening, and wherein at least one of the plurality of planes of occlusion at the proximal or distal ends has a larger cross-sectional area than the at least one central plane of occlusion in the expanded preset configuration.

27. The medical device of claim 26, wherein at least one of the plurality of planes of occlusion at the proximal end is configured to be positioned within a first vessel or an organ, at least one of the plurality of planes of occlusion at the distal end is configured to be positioned within a second vessel or an organ, and the at least one central plane of occlusion is configured to be positioned within an opening extending between the first and second vessels or organs.

28. The medical device of claim 26, wherein at least one of the plurality of layers of braided metal fabric comprises Nitinol.

29. The medical device according to claim 26, wherein at least one of the plurality of planes of occlusion of the disks or the at least one central plane of occlusion is oval or crescent shaped in cross section.

30. The medical device according to claim 26, wherein at least one of the plurality of planes of occlusion of the disks or the at least one central plane of occlusion is non-circular in shape in cross section.

31. A medical device for occluding an abnormality, the medical device comprising:

an expanded preset configuration having proximal and distal ends, the expanded preset configuration comprising a disk at each of the proximal and distal ends and a central portion disposed between the disks, each of the disks and the central portion disposed along a central axis extending between the proximal and distal ends, wherein each of the disks comprises a plurality of planes of occlusion and the central portion comprises at least one central plane of occlusion, at least one of the planes of occlusion of the disks or the central portion comprising a plurality of separate layers of braided metal fabric, wherein the medical device is configured to be delivered through a catheter having an outer diameter of less than 9 French for percutaneous delivery to the vascular abnormality, and wherein each of the planes of occlusion of the disks and the central portion is oriented generally transverse to the central axis and is configured to be oriented generally transverse to blood flow such that the layers of braided metal fabric are configured to substantially occlude blood flow therethrough so as to occlude the abnormality, and wherein at least one of the plurality of planes of occlusion at the proximal or distal ends has a larger cross-sectional area than the at least one central plane of occlusion in the expanded preset configuration.

32. The medical device of claim 31, wherein the medical device is configured to be delivered through a catheter having an outer diameter of less than 7 French for percutaneous delivery to the vascular abnormality.

33. The medical device of claim 31, wherein the medical device is configured to be delivered through a catheter having an outer diameter of less than 6 French for percutaneous delivery to the vascular abnormality.

34. The medical device of claim 31, wherein the medical device is configured to be delivered through a catheter having an outer diameter of less than 5 French for percutaneous delivery to the vascular abnormality.

35. The medical device of claim 31, wherein at least one of the plurality of layers of braided metal fabric comprises Nitinol.

36. A medical device for occluding an abnormality, the medical device comprising:

an expanded preset configuration having proximal and distal ends, the expanded preset configuration comprising a disk at each of the proximal and distal ends and a central portion disposed between the disks, wherein each of the disks comprises a plurality of planes of occlusion and the central portion comprises at least one central plane of occlusion, at least one of the planes of occlusion of the disks or the central portion comprising a plurality of separate layers of braided metal fabric, wherein each of the planes of occlusion of the disks and the central portion is configured to be oriented generally transverse to blood flow such that the layers of braided metal fabric are configured to substantially occlude blood flow therethrough so as to occlude the abnormality in less than about 10 minutes, wherein at least one of the plurality of planes of occlusion at the proximal or distal ends has a larger cross-sectional area than the at least one central plane of occlusion in the expanded preset configuration, the medical device further comprising:

a waist extending between one of the plurality of planes of occlusion at the proximal or distal end and the at least one central plane of occlusion, the waist having a smaller cross-sectional area than both the one of the plurality of planes of occlusion at the proximal or distal end and the at least one central plane of occlusion, and wherein the one of the plurality of planes of occlusion at the proximal or distal ends is configured to articulate with respect to the at least one central plane of occlusion about the waist.

* * * * *

UNITED STATES PATENT AND TRADEMARK OFFICE
CERTIFICATE OF CORRECTION

| | | |
|---|---|---|
| PATENT NO. | : 8,313,505 B2 | Page 1 of 1 |
| APPLICATION NO. | : 12/040260 | |
| DATED | : November 20, 2012 | |
| INVENTOR(S) | : Amplatz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 501 days.

Signed and Sealed this
Nineteenth Day of May, 2015

Michelle K. Lee
*Director of the United States Patent and Trademark Office*